United States Patent
Guilford et al.

(10) Patent No.: US 10,052,089 B2
(45) Date of Patent: Aug. 21, 2018

(54) DEVICE AND METHOD FOR SAFELY EXPANDING MINIMALLY INVASIVE SURGICAL INCISIONS

(75) Inventors: William H. Guilford, Charlottesville, VA (US); Craig L. Slingluff, Jr., Charlottesville, VA (US); Joshua M. Judge, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 299 days.

(21) Appl. No.: 13/883,206

(22) PCT Filed: Nov. 4, 2011

(86) PCT No.: PCT/US2011/059379
§ 371 (c)(1),
(2), (4) Date: May 2, 2013

(87) PCT Pub. No.: WO2012/061738
PCT Pub. Date: May 10, 2012

(65) Prior Publication Data
US 2013/0231538 A1 Sep. 5, 2013

Related U.S. Application Data

(60) Provisional application No. 61/410,040, filed on Nov. 4, 2010.

(51) Int. Cl.
*A61B 17/02* (2006.01)
*A61B 17/32* (2006.01)

(52) U.S. Cl.
CPC .. *A61B 17/02* (2013.01); *A61B 2017/320052* (2013.01)

(58) Field of Classification Search
CPC ........ A61B 17/02; A61B 2017/320052; A61B 1/32; A61B 1/07; A61B 17/0218; A61B 1/0676; A61B 19/5202
See application file for complete search history.

(56) References Cited

U.S. PATENT DOCUMENTS

| | | | |
|---|---|---|---|
| 659,182 | A | 10/1900 | Pilling |
| 1,465,259 | A | 8/1923 | Friedman |

(Continued)

FOREIGN PATENT DOCUMENTS

| | | |
|---|---|---|
| DE | 29804516 U1 | 5/1998 |
| WO | WO-92000773 | 1/1992 |

(Continued)

OTHER PUBLICATIONS

Bordelon, B, "Incision extension is the optimal method of difficult gallbladder extraction at laparoscopic cholecystectomy", Surgical Endoscopy, 6 (5), (1992), 225-227.

(Continued)

*Primary Examiner* — Christopher Beccia
(74) *Attorney, Agent, or Firm* — Robert J. Decker

(57) ABSTRACT

An insertion tongue of the retractor device may be pushed into the subject through the trocar incision, along one side of the organ. The tip of the insertion tongue pushes the impacted organ and its endoscopic recovery bag slightly away from the cavity wall. A scalpel is passed through the insertion guide with the tip of the scalpel blade in the retention guide on the back of the insertion tongue, and with the sharp side of the scalpel blade facing away from the organ and from the tongue of the retractor device. The scalpel is then passed down through the cavity wall, with its tip in the retention guide, while tension on the retractor device handle away from the organ, and gentle outward traction on the organ (and bag) permits removal of the organ (and bag) as soon as the opening is just large enough to allow it.

29 Claims, 14 Drawing Sheets

(56) References Cited

U.S. PATENT DOCUMENTS

| | | | |
|---|---|---|---|
| 2,863,444 A | 12/1958 | Joseph | |
| 4,232,660 A * | 11/1980 | Coles | A61B 17/02 600/205 |
| 4,610,243 A | 9/1986 | Ray | |
| 4,836,190 A | 6/1989 | Zwick | |
| 4,945,897 A | 8/1990 | Greenstein | |
| 5,351,680 A | 10/1994 | Jung | |
| 5,375,591 A | 12/1994 | Mouret | |
| 5,514,077 A | 5/1996 | Rabban | |
| 5,522,791 A | 6/1996 | Leyva | |
| 5,558,621 A | 9/1996 | Heil | |
| 5,558,622 A | 9/1996 | Greenberg | |
| 5,667,519 A | 9/1997 | Ramsey | |
| 5,746,743 A | 5/1998 | Greenberg | |
| 6,007,554 A | 12/1999 | Van Ess | |
| 6,354,994 B1 | 3/2002 | Rullo | |
| 6,416,465 B2 | 7/2002 | Brau | |
| 6,554,768 B1 | 4/2003 | Leonard | |
| 6,732,739 B2 | 5/2004 | Cosgrove | |
| 6,740,102 B2 * | 5/2004 | Hess | A61B 17/00008 600/114 |
| 7,220,228 B2 | 5/2007 | Hu | |
| D568,471 S | 5/2008 | Engler | |
| 7,396,328 B2 * | 7/2008 | Penenberg | A61B 1/32 600/201 |
| 2003/0195392 A1 | 10/2003 | Hamel | |
| 2004/0225192 A1 * | 11/2004 | Young | A61B 17/34 600/204 |
| 2004/0254428 A1 | 12/2004 | Ritland | |
| 2005/0228233 A1 * | 10/2005 | Ritland | A61B 17/02 600/210 |
| 2006/0052672 A1 | 3/2006 | Landry | |
| 2006/0063978 A1 | 3/2006 | Ritland | |
| 2006/0189848 A1 | 8/2006 | Penenberg | |
| 2009/0048620 A1 | 2/2009 | Weiss | |
| 2010/0234687 A1 | 9/2010 | Azarbarzin | |
| 2011/0054258 A1 * | 3/2011 | O'Keefe | A61B 17/3423 600/206 |
| 2012/0116170 A1 * | 5/2012 | Vayser | A61B 1/0676 600/203 |

FOREIGN PATENT DOCUMENTS

| | | |
|---|---|---|
| WO | WO-02060330 | 8/2002 |
| WO | WO-2004006778 | 1/2004 |
| WO | WO-2011087462 | 7/2011 |

OTHER PUBLICATIONS

Kim, J, "Unsuspected Gallbladder Cancer Diagnosed After Laparoscopic Cholecystectomy: Focus on Acute Cholecystitis", World Journal of Surgery, 34 (1), (2010), 114-120.

Olsen, D. O., "Laparoscopic cholecystectomy", The American Journal of Surgery, 161 (3), (1991), 339-344.

Sarli, L, "Does Laparoscopic Cholecystectomy Worsen the Prognosis of Unsuspected Gallbladder Cancer?", Arch Surg, 135 (11), (2000), 1340-1344.

Wullstein, C, "Do complications related to laparoscopic cholecystectomy influence the prognosis of gallbladder cancer?", Surgical Endoscopy, 16 (5), (2002), 828-832.

* cited by examiner

DEVICE AND METHOD FOR SAFELY EXPANDING MINIMALLY INVASIVE SURGICAL INCISIONS

RELATED APPLICATIONS

This application is a national stage filing of International Application No. PCT/US2011/059379, filed Nov. 4, 2011, which claims the benefit of priority under 35 U.S.C. Section 119(e) from U.S. Provisional Application Ser. No. 61/410,040 filed Nov. 4, 2011, entitled "Laparo-Extender Device and Method for Safely Expanding Laparoscopic Surgical Incisions;" the disclosures of which are hereby incorporated by reference herein in their entirety.

FIELD OF THE INVENTION

The present invention relates generally to the field of medical devices to be used for minimally invasive procedures. More specifically, the invention is in the subfield of retractor devices and other related tools to be used for surgical procedure types such as laparoscopic, thoracic, or endoscopic.

BACKGROUND OF THE INVENTION

With an estimated 500,000 minimally invasive cholecystectomies performed each year, laparoscopic cholecystectomy is one of the most common general surgical procedures performed. See Olsen D O. Laparoscopic cholecystectomy. *The American Journal of Surgery* 1991; 161(3):339-344, of which is hereby incorporated by reference herein in its entirety. Operative times are low with good outcomes; however, one source of frustration commonly encountered involves extraction of the gallbladder from the patient's abdomen through an incision often smaller than the gallbladder itself. Typical maximum port size (used to access the inside of the abdomen) in laparoscopic cholecystectomy is 10-14 mm, while stone-filled and inflamed gallbladders may be larger than 4 cm in diameter.

Not every laparoscopic cholecystectomy is associated with a prolonged extraction. However, in difficult cases the awkward maneuvers in conjunction with repeat attempts can lead to lengthened operative times, with increased cost to the patient and the institution. There is little in the literature regarding what proportion of patients undergoing laparoscopic cholecystectomy will experience prolonged extraction; however anecdotal estimates indicate 20-30% of patients will have this problem which may be as high as 50% at some institutions. This difficult problem may add 20 minutes or more to a procedure which otherwise can take as little as one hour. Operating room time is expensive; current estimates of cost is about $30 per minute, thus saving 20 minutes could save over $600.

The gallbladder is filled with bile, which often is infected in patients with cholecystitis. Bile that spills into the abdomen is irritating and can cause inflammatory changes and result in infection. Anecdotal cases support concern about the associated risk, thus it is common surgical practice to avoid bile spillage whenever possible. Bile spillage is particularly undesirable in patients harboring a gallbladder cancer because of concern for port site or peritoneal metastasis. See Sarli L, Contini S, Sansebastiano G, Gobbi S, Costi R, Roncoroni L. Does Laparoscopic Cholecystectomy Worsen the Prognosis of Unsuspected Gallbladder Cancer? *Arch Surg* 2000; and 135(11):1340-1344, and Wullstein C, Woeste G, Barkhausen S, Gross E, Hopt U. Do complications related to laparoscopic cholecystectomy influence the prognosis of gallbladder cancer? *Surgical Endoscopy* 2002; 16(5):828-832, of which are hereby incorporated by reference herein in their entirety. This diagnosis of cancer often is not made until post-operative pathologic examination; thus spillage risk must be minimized for all patients. See Kim J, Kim W, Kim J, Yoo B, Kim M. Unsuspected Gallbladder Cancer Diagnosed After Laparoscopic Cholecystectomy: Focus on Acute Cholecystitis. *World Journal of Surgery* 2010; 34(1):114-120, of which is hereby incorporated by reference herein in its entirety.

Few studies have attempted to discern the optimal method for gallbladder extraction from the abdominal cavity; however, one study found incision extension to result in no increase in morbidity. See Bordelon B, Hobday K, Hunter J. Incision extension is the optimal method of difficult gallbladder extraction at laparoscopic cholecystectomy. *Surgical Endoscopy* 1992; 6(5):225-227, of which is hereby incorporated by reference herein in its entirety. Unfortunately, such extension is often technically awkward and entails significant risk to the patient, because available tools are not designed for this purpose other than the endoscopic bags that are used to contain the tissue as it is pulled through the abdominal wall. Other methods currently employed by surgeons include stretching of the incision using brute force, also without specially designed tools. Collectively, these approaches can result in sequelae of stretching such as bruising and excessive pain, or may result in puncture of the specimen bag, which should be avoided given the associated risks mentioned above.

The concept of incision extension to retrieve the surgical specimen during laparoscopic surgery is applicable to a wide variety of uses. Essentially any operation in which a specimen larger than the largest operative port utilized needs to be retrieved from a body cavity, or a specimen which needs to be retrieved intact, benefits from a technique allowing controlled incision extension. This includes but is not limited to laparoscopic appendectomy, splenectomy, partial or total gastrectomy, nephrectomy, adrenalectomy, colectomy, enterectomy, esophagectomy, liver resection, oophorectomy, and pancreatectomy. The concept also applies for endoscopic removal of organs or tissues from a body cavity, including thoracoscopic surgery, and removal of lung tissue, pleural masses, or other intrathoracic structures.

SUMMARY OF EXEMPLARY EMBODIMENTS OF THE INVENTION

As a brief general overview, a use by a surgeon of an embodiment of the retractor device may include, for example, when it is apparent that the gallbladder is too large to pull easily through the trocar site (e.g., cavity wall incision). Accordingly, in practice the surgeon may proceed by pushing the insertion tongue (e.g., distal portion) of the retractor device into the subject through the trocar incision, along one side of the gallbladder (typically along the side of the bag in which the gallbladder is held). The tip of the insertion tongue (distal portion) pushes the impacted gall bladder (or other organ) and its endoscopic recovery bag slightly away from the abdominal wall. A surgical tool (e.g., scalpel) is passed through the scalpel guide (aperture) with the tip of the scalpel blade in the retention groove on the back of the insertion tongue (distal portion), and with the sharp side of the scalpel blade facing away from the gallbladder and from the tongue (distal portion) of the retractor device. The scalpel is then passed down through the abdominal wall, with its tip in the retention groove, while tension on the retractor device handle away from the gallbladder, and gentle outward traction on the gallbladder (and bag) permits removal of the gallbladder (and bag) as soon as the opening is just large enough to allow it. This step may be repeated if the gallbladder cannot be removed after a single passage of the scalpel. The retractor device also may be removed before the gallbladder and its bag are pulled through the enlarged incision. When properly used, the design of the retractor device mitigates the risk of accidentally cutting the recovery bag and/or organ as the incision is enlarged, and also keeps the opening occluded to prevent decompression of the abdominal cavity, thus keeping the abdominal wall and the scalpel blade used to extend the incision well away from abdominal contents.

An aspect of an embodiment of the present invention provides an apparatus comprising a surgical retractor device for insertion through an incision in a cavity wall of a subject for use with a surgical tool. The surgical retractor device comprises a refraction member having a proximal portion and a distal portion. Further, the proximal portion may comprise an aperture in communication therewith, whereby the aperture may be configured to accommodate at least a portion of the surgical tool for insertion there through. Further, the distal portion may be configured to protect a target region of the subject by blocking and displacing the target region away from the surgical tool to be passed through the proximal portion aperture.

An aspect of an embodiment of the present invention provides a method for inserting a surgical retractor device through an incision in a cavity wall of a subject for use with a surgical tool. The method may comprise: 1) obtaining or providing the surgical retractor device that includes a retraction member having a proximal portion and a distal portion, wherein the proximal portion comprises an aperture in communication therewith, and wherein the distal portion is configured to protect a target region of the subject by blocking and displacing the target region away from the surgical tool to be passed through the proximal portion aperture; 2) inserting at least a portion of the surgical tool through the proximal portion aperture; and 3) using the distal portion for blocking and displacing the target region away from the portion of the surgical tool that is passed through the proximal portion aperture.

An aspect of an embodiment of the present invention provides an apparatus comprising: a surgical tool; and a surgical retractor device for insertion through an incision in a cavity wall of a subject. The surgical retractor device may comprise a retraction member having a proximal portion and a distal portion. The proximal portion may comprise an aperture in communication therewith, whereby thee aperture may be configured to accommodate at least a portion of the surgical tool for insertion there through. The distal portion may be configured to protect a target region of the subject by blocking and displacing the target region away from the surgical tool to be passed through the proximal portion aperture.

An aspect of an embodiment of the present invention provides an apparatus comprising: a surgical retractor device for insertion through an incision in a cavity wall of a subject for use with a surgical tool. The surgical retractor device may comprise a retraction member having a proximal portion and a distal portion. Further, the proximal portion may comprise an insertion guide in communication therewith, whereby the insertion guide may be configured to accommodate at least a portion of the surgical tool for insertion there through. The distal portion may be configured to protect a target region of the subject by blocking and displacing the target region away from the surgical tool to be passed through the proximal portion aperture.

An aspect of an embodiment provides an insertion tongue of the retractor device may be pushed into the subject through the trocar incision, along one side of the organ (such as along the side of a bag in which the organ may be held). The tip of the insertion tongue pushes the impacted organ and its endoscopic recovery bag slightly away from the cavity wall. A scalpel is passed through the insertion guide (scalpel guide) with the tip of the scalpel blade in the retention guide on the back of the insertion tongue, and with the sharp side of the scalpel blade facing away from the organ and from the tongue of the retractor device. The scalpel is then passed down through the cavity wall, with its tip in the retention guide, while tension on the retractor device handle away from the organ, and gentle outward fraction on the organ (and bag) permits removal of the organ (and bag) as soon as the opening is just large enough to allow it. The retractor device also may be removed before the organ and its bag are pulled through the enlarged incision.

These and other objects, along with advantages and features of various aspects of embodiments of the invention disclosed herein, will be made more apparent from the description, drawings and claims that follow.

BRIEF DESCRIPTION OF THE DRAWINGS

The accompanying drawings, which are not necessarily drawn to scale, and which are incorporated into and form a part of the instant specification, illustrate several aspects and embodiments of the present invention and, together with the description herein, serve to explain the principles of the invention. The drawings are provided only for the purpose of illustrating select embodiments of the invention and are not to be construed as limiting the invention.

DETAILED DESCRIPTION OF EXEMPLARY EMBODIMENTS OF THE INVENTION

Figures 1A, 1B:
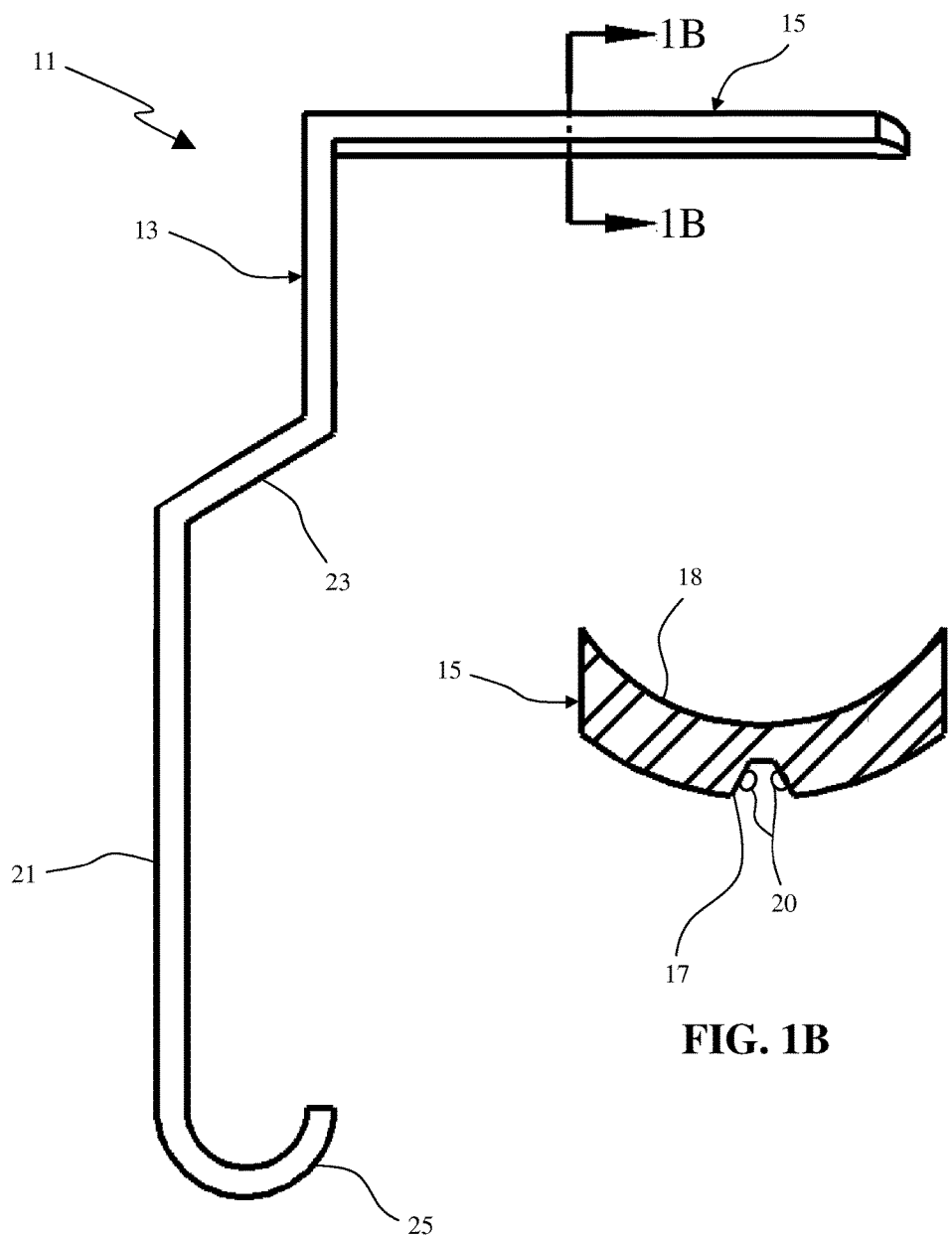
FIG. 1A provides a side view of an embodiment of the surgical retractor.
FIG. 1B provides a cross-sectional view of the surgical retractor as illustrated in FIG. 1A.
Figure 2A:
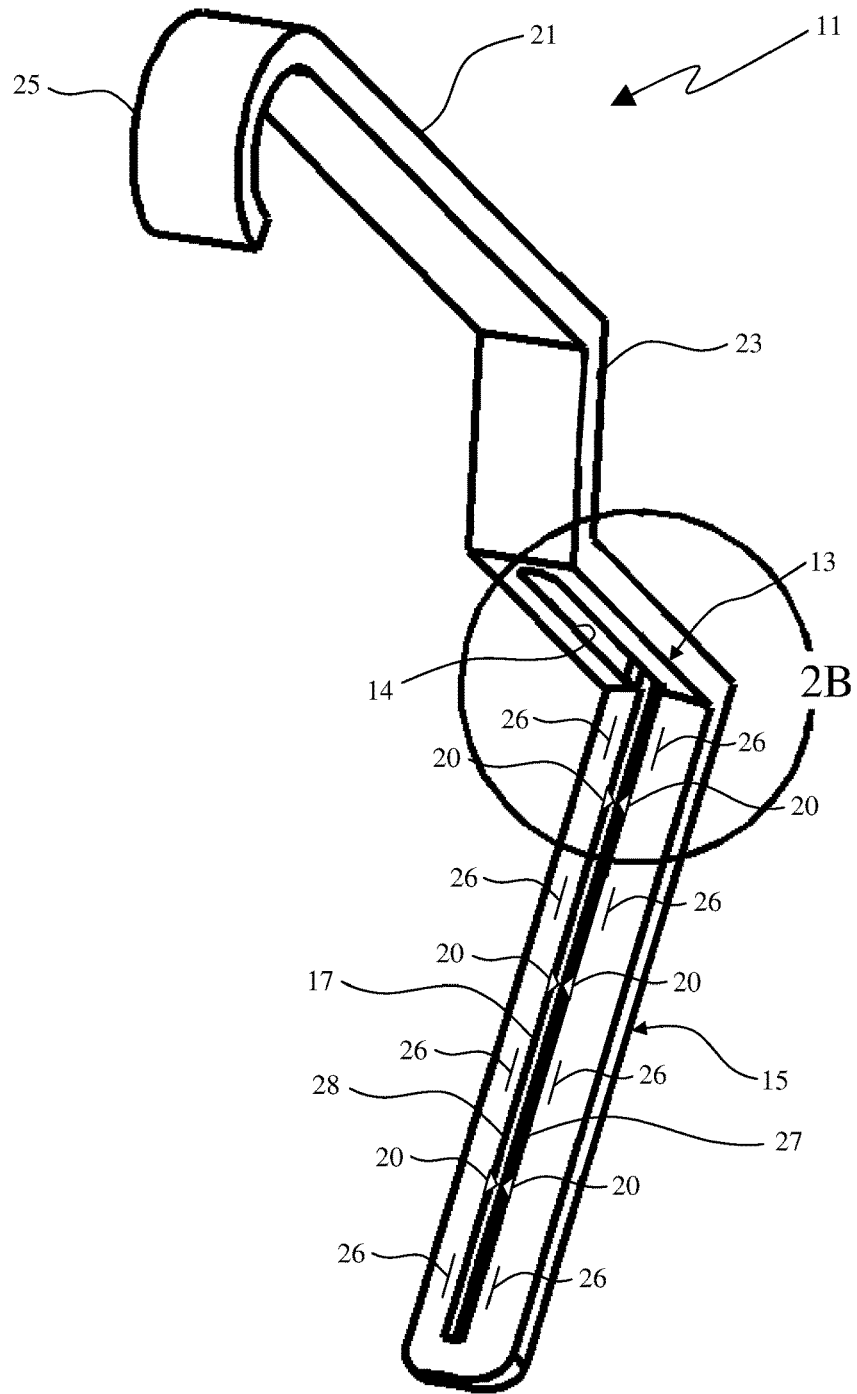
FIG. 2A provides a perspective bottom view of an embodiment of the surgical retractor.
Figure 2B:
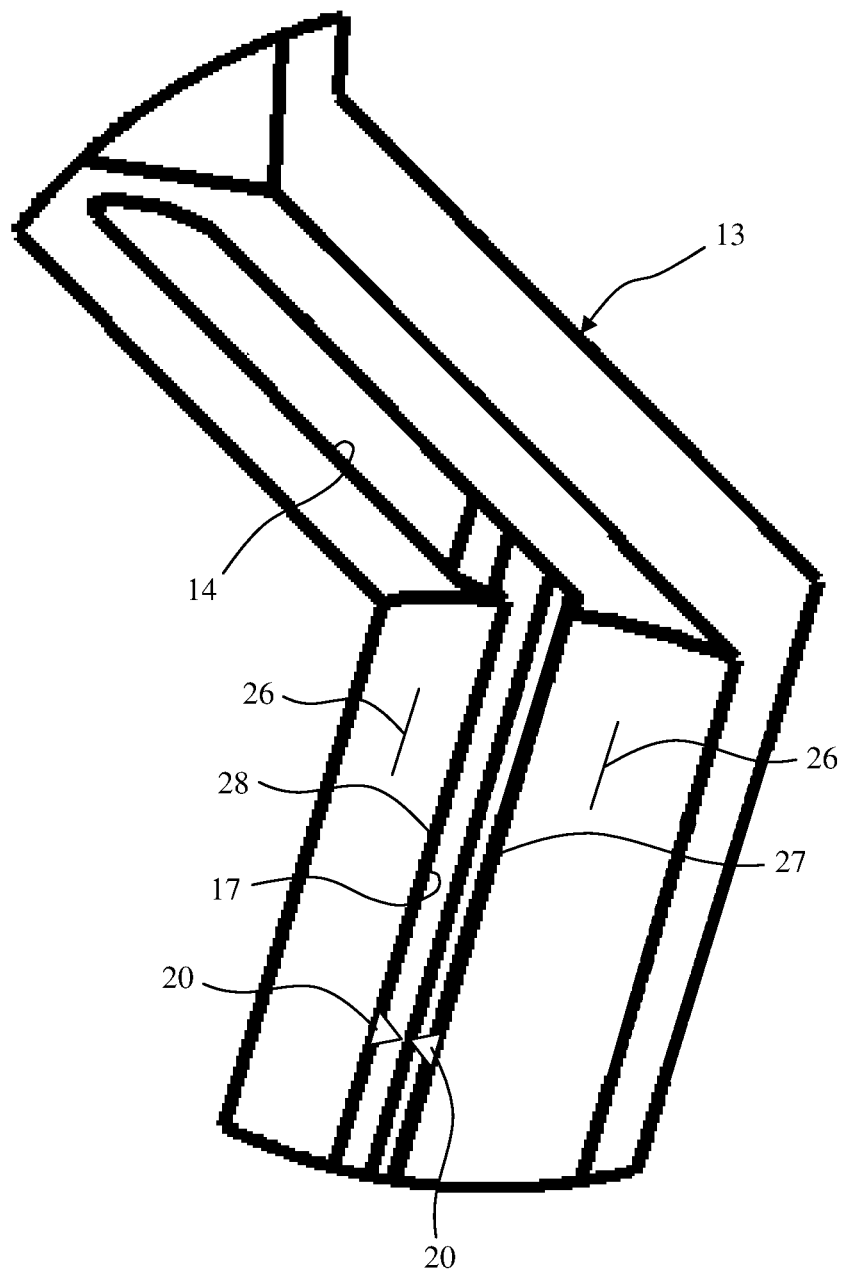
FIG. 2B provides an exploded partial view of the surgical retractor as identified in FIG. 2A.
Figures 3A, 3B:
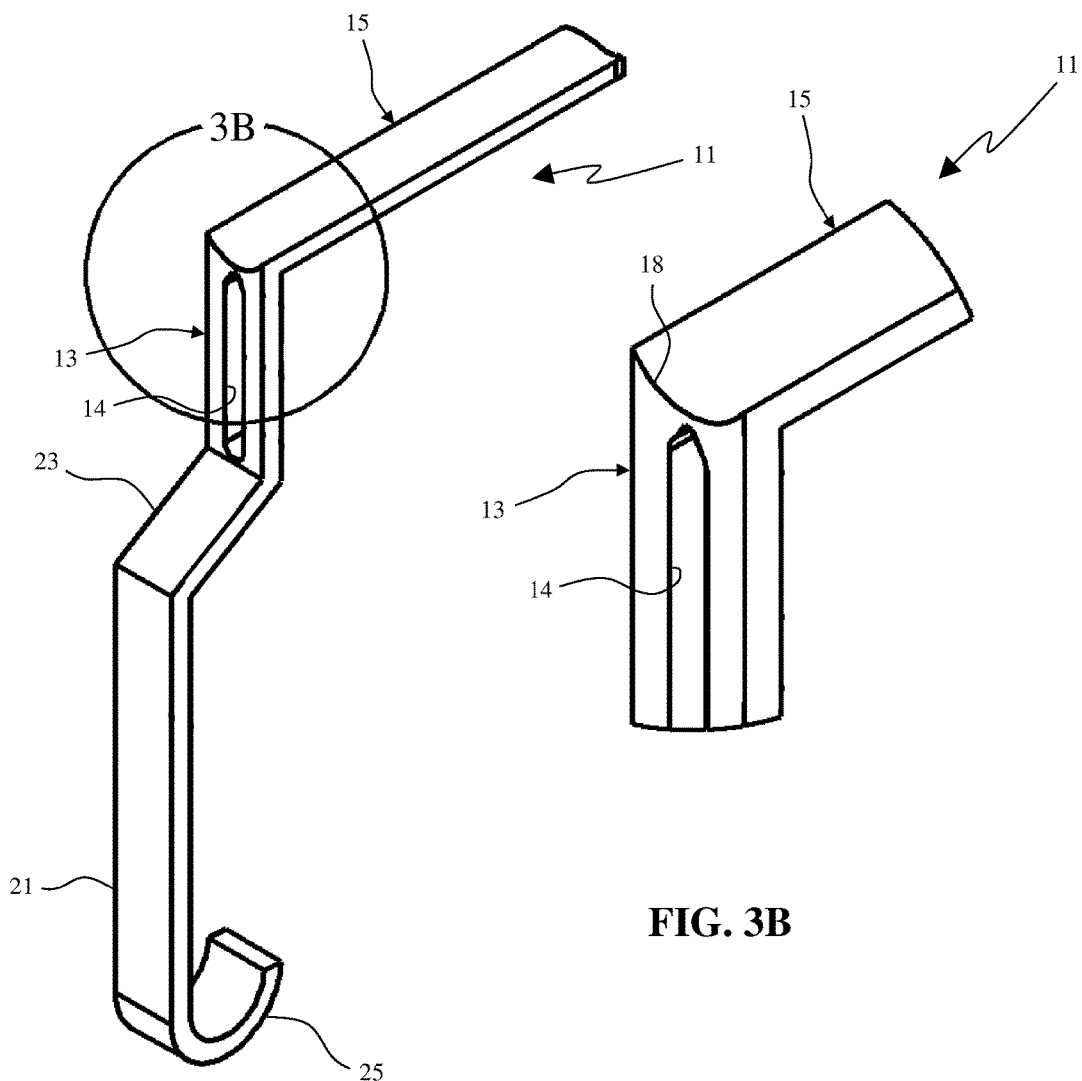
FIG. 3A provides a perspective side view of an embodiment of the surgical retractor.
FIG. 3B provides an exploded partial view of the surgical retractor as identified in FIG. 3A.
Figures 4A, 4B:
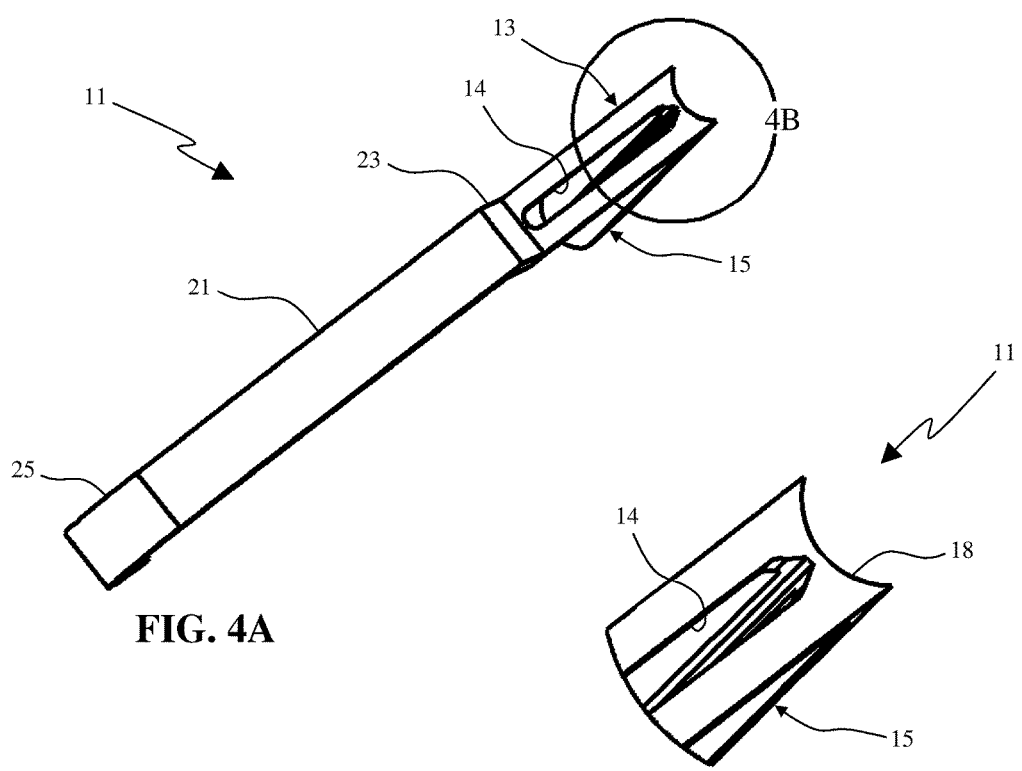
FIG. 4A provides a perspective top view of an embodiment of the surgical retractor.
FIG. 4B provides an exploded partial view of the surgical retractor as identified in FIG. 4A.
Figure 5A:
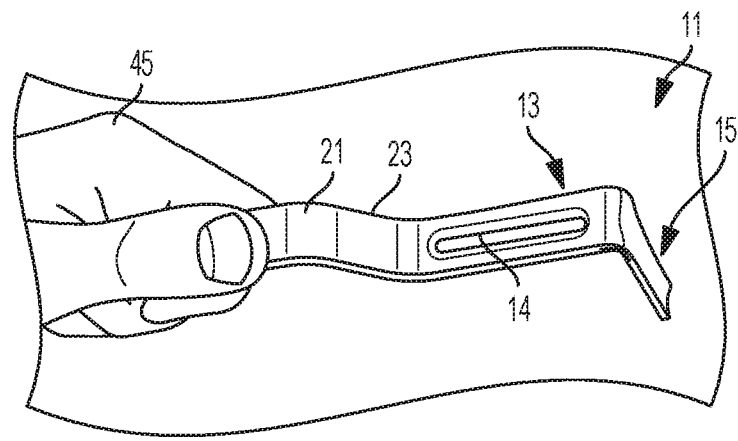
FIG. 5A provides a photographic depiction of a top view of an embodiment of the surgical retractor while in the grasp of user.
Figure 5B:
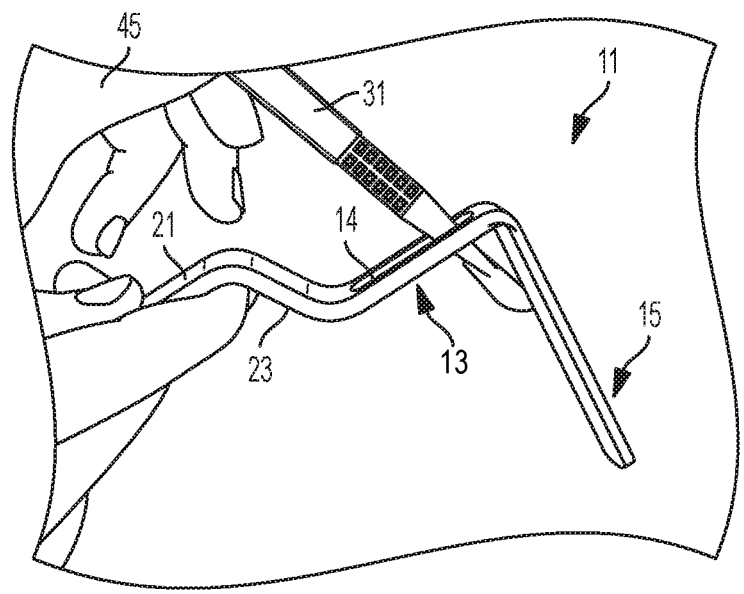
FIG. 5B provides a photographic depiction of a side view of an embodiment of the surgical retractor while in the grasp of user, and wherein a surgical tool is inserted therein.
Figure 13:
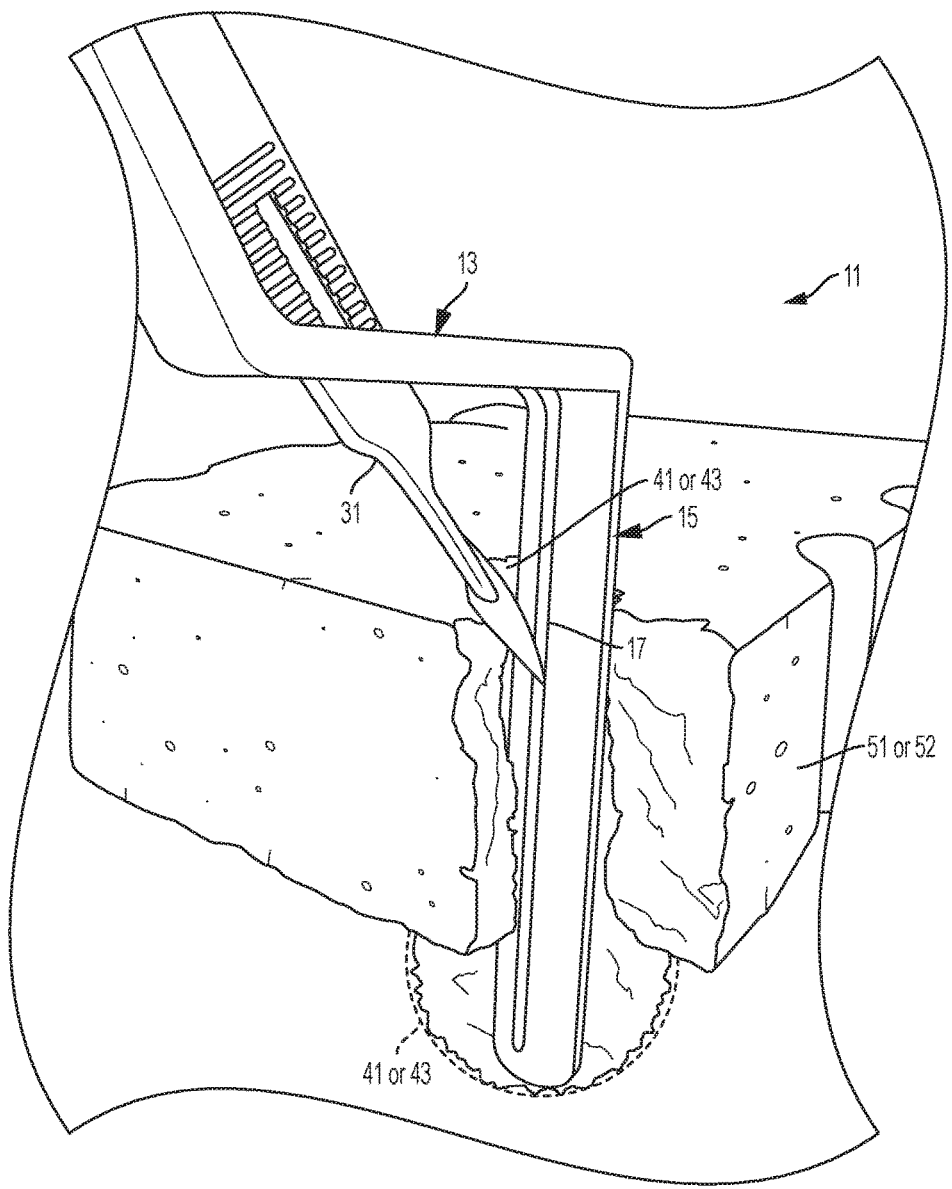
FIG. 13 provides a photographic depiction of perspective view of an embodiment of the surgical retractor having a surgical tool inserted through its aperture and in communication with its retention groove while the surgical retractor is inserted into a model cavity wall or abdominal wall adjacent to a model container (or may be organ directly) for an organ.

Turning to the figures, FIG. 1A provides a side view of an embodiment of the surgical retractor. FIG. 1B provides a cross-sectional view the surgical retractor as depicted in FIG. 1A. FIG. 2A provides a perspective bottom view of an embodiment of the surgical retractor. FIG. 2B provides an exploded partial view of the surgical retractor as depicted in FIG. 2A. FIG. 3A provides a perspective side view of an embodiment of the surgical retractor. FIG. 3B provides an exploded partial view of the surgical retractor as depicted in FIG. 3A. FIG. 4A provides a perspective top view of an embodiment of the surgical retractor. FIG. 4B provides an exploded partial view of the surgical retractor as depicted in FIG. 4A. FIG. 5A provides a photographic depiction of top view of an embodiment of the surgical retractor while in the grasp of user. FIG. 5B provides a photographic depiction of side view of an embodiment of the surgical retractor while in the grasp of user and a surgical tool inserted therein. FIG. 13 provides a photographic depiction of perspective view of an embodiment of the surgical refractor having a surgical tool inserted through its aperture and in communication with its retention groove while the surgical retractor is inserted into a model cavity wall or abdominal wall adjacent to a model container for an organ (or may be an organ without the existence of a bag or container).

Still referring to FIGS. 1-5 and 13, an aspect of an embodiment of the present invention provides a surgical member 11 of a surgical refractor device for insertion through an incision in a cavity wall 51 (for example an abdominal wall 52) of a subject for use with a surgical tool 31 (for example a scalpel 32). The surgical retractor device may comprise a retraction member 11 having a proximal portion 13 and a distal portion 15 (such as a tongue or the like). The proximal portion 11 includes an aperture 14 (or suitable slot or recess) that is configured to accommodate the surgical tool 31 that is grasped by a user 45 (for example a surgeon). Additionally, the proximal portion 13 may further comprises a handle 21 or be in communication with a handle or the like. The handle 21 may be configured with or in communication with a catch 25 configured to help the user 45 grasp or control the handle 21.

The distal portion is configured to protect an organ 41 (or a bag/container 43 or both the organ and bag/container) of the subject by blocking and displacing the organ (and/or bag/container) away from the surgical tool 31 that is inserted through the aperture 14. The distal portion may include a retention guide 17 (or the like) that is configured to receive and guide a portion of the surgical tool that has been inserted in the aperture. Further, the retention guide may be designed to provide a configuration so as to prevent the surgical tool from contacting the organ (and/or bag/container). Further the retractor device provides a configuration whereby the aperture and retention guide are aligned with one another so as to be able to simultaneously accommodate the inserted surgical tool in the aperture and retention groove.

It should be appreciated that the retention guide may be a variety of systems, devices, mechanisms, surfaces, and structures (or any combination thereof). For instance, the retention guide 17 may be, but not limited thereto, a groove, slot, track or channel (or any combination thereof). For instance, the retention guide 17 may include a trolley mechanism or the like in communication with the distal portion, whereby the trolley mechanism may be configured to travel in communication along the distal portion 15.

It should be appreciated that an insertion guide may be used instead of the aperture 14 in the proximal portion 13 (or some combination of the insertion guide and aperture). For instance, the retention guide (not shown) may include, but is not limited thereto, the following: recess, post, tab, hook, notch, cut, slot, holder or socket (or some combination thereof) configured to control the movement of the surgical tool relative to the surgical retractor device (such as the distal portion), as well as the target region, organ, tissue or bag/container. The insertion guide may be disposed directly to or in communication with the retractor device, such as at the proximal portion, handle, off-set member, distal portion, or any suitable, desired or required location.

Still referring to FIGS. 1-5 and 13, in an approach the proximal portion may comprise one or more offset members 23 (or segments); or may be in communication with one or more offset members.

The proximal portion and distal portion provides a configuration such that during use it helps to guide and extend the incision of the cavity wall. The cavity wall may be, but not limited thereto, an abdominal wall, pelvic wall, or thoracic wall. Similarly, the surgical incision is a type that may be provided by, but not limited thereto, one of the following surgical procedure types: laparoscopic, thoracic, or endoscopic. The surgical tool to be used with the various embodiments of the present invention surgical retractor may include, but not limited thereto, one of the following: scalpel, other cutting instrument, cautery instrument, and needle.

As reflected by the various embodiments illustrated and disclosed herein, the aperture 13 is disposed within the proximal portion. However, it should be appreciated that there may be a plurality of apertures (or recesses) to accommodate one or more surgical tools. Additionally, each aperture may be sized or shaped to accommodate more than one surgical tool or type of surgical tool. Moreover, the aperture, slot or recess, may be in communication adjacent to the proximal portion rather than spanning within or across the surface of the aperture itself.

As reflected by the various embodiments illustrated and disclosed herein, the retention guide 17, such as a groove, is disposed within the distal portion. However, it should be appreciated that there may be a plurality of retention guides (or other types of grooves or tracks or suitable guiding structures) to accommodate one or more surgical tools. Moreover, the retention guide (or grooves or other types of tracking or guiding structures, surfaces, contours or arrangements) may be in communication adjacent to the distal portion rather than spanning within or across the surface of the distal portion itself.

Still referring to FIGS. 1-5 and 13, an aspect of an embodiment of the present invention provides a surgical retractor device that may include one or more check structures 20 in communication with the retention guide. The check structures 20 are configured to contact the surgical tool 31 traveling along the retention guide 17, wherein the contact provides feedback (for example, but not limited thereto, tactile, electromechanical, or electronic feedback) to the user of the corresponding location of the surgical tool in reference to the retention guide (e.g., groove) and/or distal portion. While the check structures 20 are illustrated in a staggered fashion it should be appreciated that they may be one continuous structure. Whether staggered or continuous, the check structures may be a variety of shapes and sizes, as well as be applied to a variety of one or more locations inside or along the retention guide (e.g., groove) as desired or required. In an embodiment, the retention guide (e.g., groove) may comprise a first side wall 27 and a second side wall 28, whereby the check structures 20 are disposed on one or both of first and second side walls of the retention guide (or in communication with the distal portion). It should be appreciated that the retention guide (e.g., groove) may be semi-cylindrical or essentially semi-cylindrical whereby essentially the two or more walls are essentially one continuous wall. Referring to FIG. 1B, although two walls may be called out it should be appreciated that the individual walls are essentially one continuous wall. The check structures may be a variety of structures including, but not limited thereto, at least one of: ridges, bumps, lips, ledges, tabs, notches, and indentations.

As shown in FIGS. 1B, 3A-B, 4A-B, and 5A, an embodiment of the surgical retractor may include a distal portion 15 that has a concave shape or surface 18, laterally across. It should be appreciated the distal portion's shape in the lateral direction may vary and certainly may included other contours, shapes, including convex, as well as straight surfaces. This equally applies to any portion, part or segment disclosed herein.

As shown in FIGS. 2A-B, an embodiment of the surgical retractor may include one or more adhesion structures 26 disposed on the surface the distal portion 15 configured to increase adhesion of the distal portion to a cavity wall. Some examples of the adhesion structures 26 may include, but not limited thereto, at least one of the following: ridges, textured surface, bumps, protrusions, and jagged surface. While the adhesion structures 26 structures are illustrated in a staggered fashion it should be appreciated that they may be one continuous structure. Whether staggered or continuous, the check structures may be a variety of shapes and sizes, as well as be applied to a variety of one or more locations as desired or required.

In an embodiment, it is contemplated that in addition to or in place of the adhesion structures, the contours of the retention guide or the catch may be configured or provided so as to increase the adhesion of the distal portion to a cavity wall.

Figure 6A:
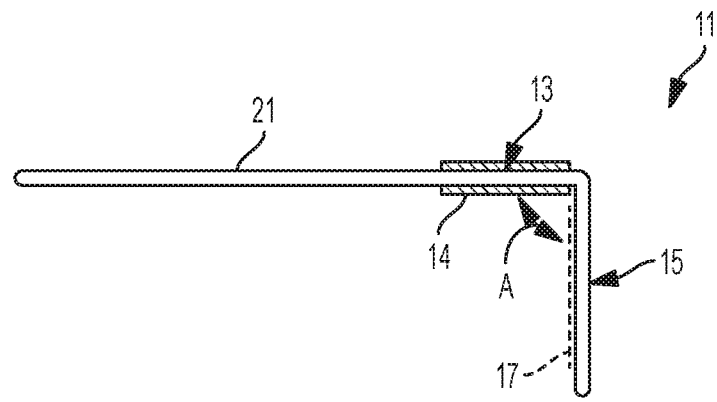
FIGS. 6A-6B provide schematic illustrations of an embodiment of the surgical retractor without an offset member and with an offset member, respectively.
Figure 6B:
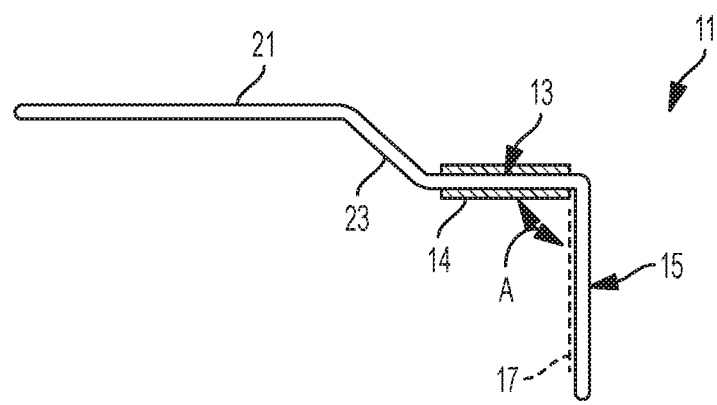

Still referring to FIGS. 1-5 and 13, an aspect of an embodiment encompasses the proximal portion 13 having a longitudinal alignment and said distal portion 15 having a longitudinally alignment wherein their respective longitudinal alignments define a general angle of about 90 degrees, as designated by angle "A". See also FIGS. 6A-B showing a similar orientation.

Figure 7A:
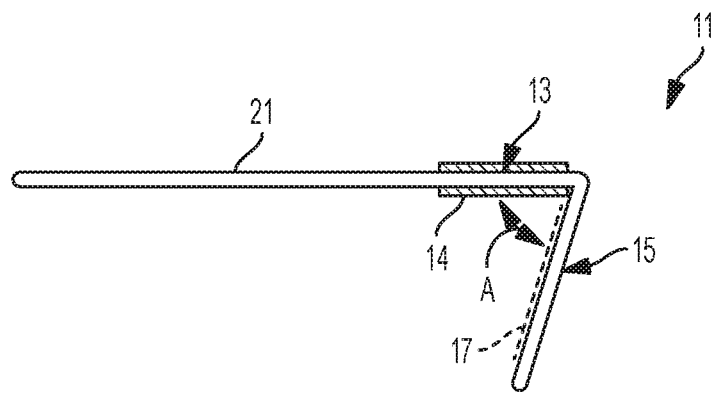
FIGS. 7A-7B provide schematic illustrations of an embodiment of the surgical retractor without an offset member and with an offset member, respectively.
Figure 7B:
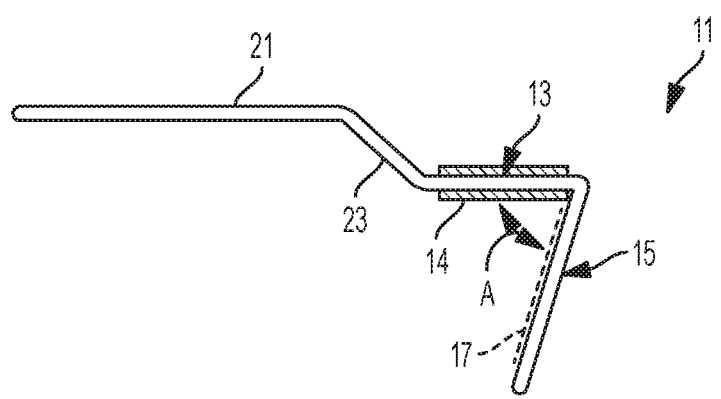

However, it should be appreciated that other orientations and alignments are feasible and therefore contemplated as part of various embodiments of the present invention. For example, referring to FIGS. 7A-B, an aspect of an embodiment encompasses the proximal portion 13 having a longitudinal alignment and said distal portion 15 having a longitudinally alignment wherein their respective longitudinal alignments define a general angle of less than about 90 degrees, as designated by angle "A".

Figure 8A:
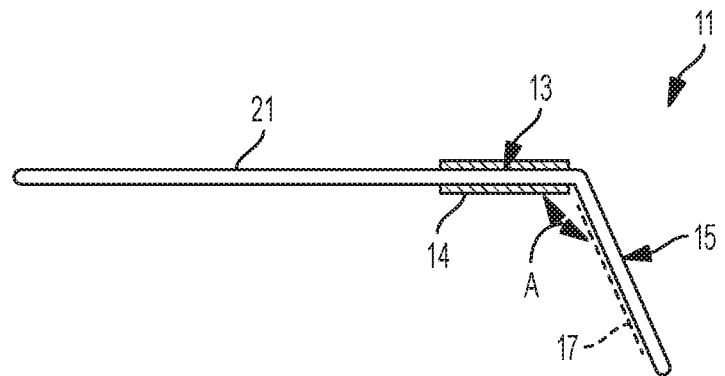
FIGS. 8A-8B provide schematic illustrations of an embodiment of the surgical retractor without an offset member and with an offset member, respectively.
Figure 8B:
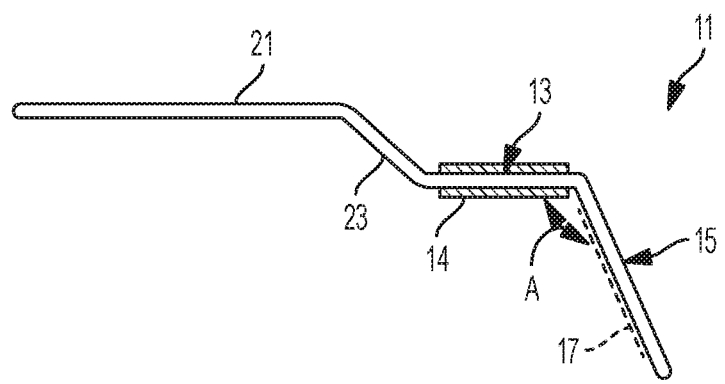

For example, referring to FIGS. 8A-B, an aspect of an embodiment encompasses the proximal portion 13 having a longitudinal alignment and said distal portion 15 having a longitudinally alignment wherein their respective longitudinal alignments define a general angle of greater than about 90 degrees, as designated by angle "A".

Moreover, it should be appreciated that an embodiment may encompass the proximal portion having a longitudinal alignment and said distal portion having a longitudinal alignment wherein their respective the longitudinal alignments define a general angle of greater than about less than 180 degrees (as well as equal to or greater than 180 degrees). It should be appreciated that any of the parts, segments, portions and structures may be angled or curved as desired or required.

Figure 9A:
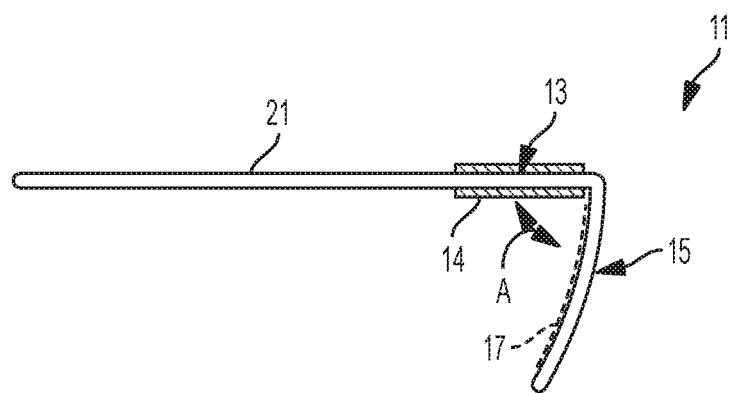
FIGS. 9A-9B provide schematic illustrations of an embodiment of the surgical retractor without an offset member and with an offset member, respectively.
Figure 9B:
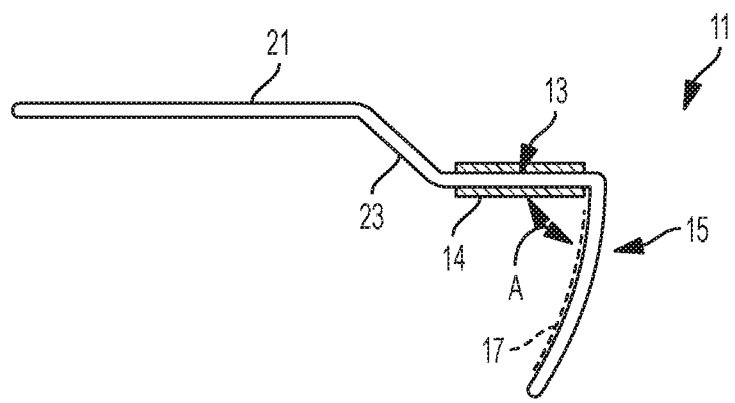
Figure 10A:
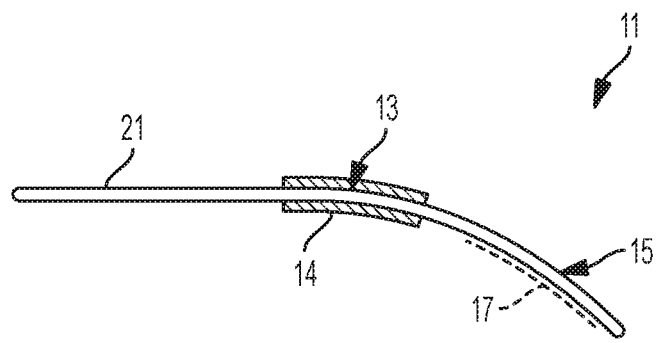
FIGS. 10A-10B provide schematic illustrations of an embodiment of the surgical retractor without an offset member and with an offset member, respectively.
Figure 10B:
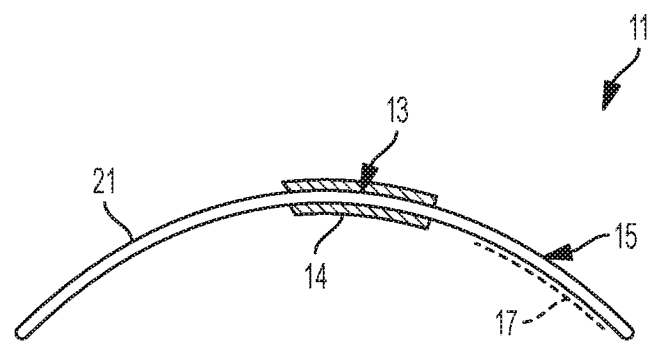

Moreover, it should be appreciated that any of the distal portions, proximal portions, handles, offset portions, or any other segments, components, extensions, or structures of the various embodiments of the present invention surgical retractor device disclosed herein may have a variety of shapes, contours, sizes, and alignments. Similarly, it should be appreciated that the distal portions, proximal portions, handles, offset portions, or any other segments, components, extensions, or structures of the various embodiments of the present invention surgical retractor device disclosed herein may can take on all shapes along the entire continual geometric spectrum of manipulation of x, y and z planes to provide and meet the anatomical, operational and structural demands and requirements. For example, referring to FIGS. 9A-B, an aspect of an embodiment encompasses a distal portion 15 having a longitudinal alignment that is generally curved, as opposed to having generally straight orientations or segments. Similarly, for example, referring to FIG. 10A an aspect of an embodiment encompasses a distal portion 15 having a longitudinal alignment that is generally curved, as opposed to having generally straight orientations or segments. Moreover, for example, referring to FIG. 10B, an aspect of an embodiment encompasses a proximal portion 13 and distal portion 15 each having longitudinal alignments that are generally curved, as opposed to having generally straight orientations or segments. It should be appreciated that any of the parts, segments, portions and structures may include multiple curves and bends within as desired or required.

It should be appreciated that any of the distal portion, proximal portion, handles, offset portion, or any other segments, components, extensions, or structures associated with the various embodiments of the present invention surgical retractor device disclosed herein may be a variety of materials, such as but not limited to, one or more of the following (or combinations thereof): stainless steel, durable steel, plastic, polymers, metal, metals, ceramics, glasses, and copolymers.

Figure 11:
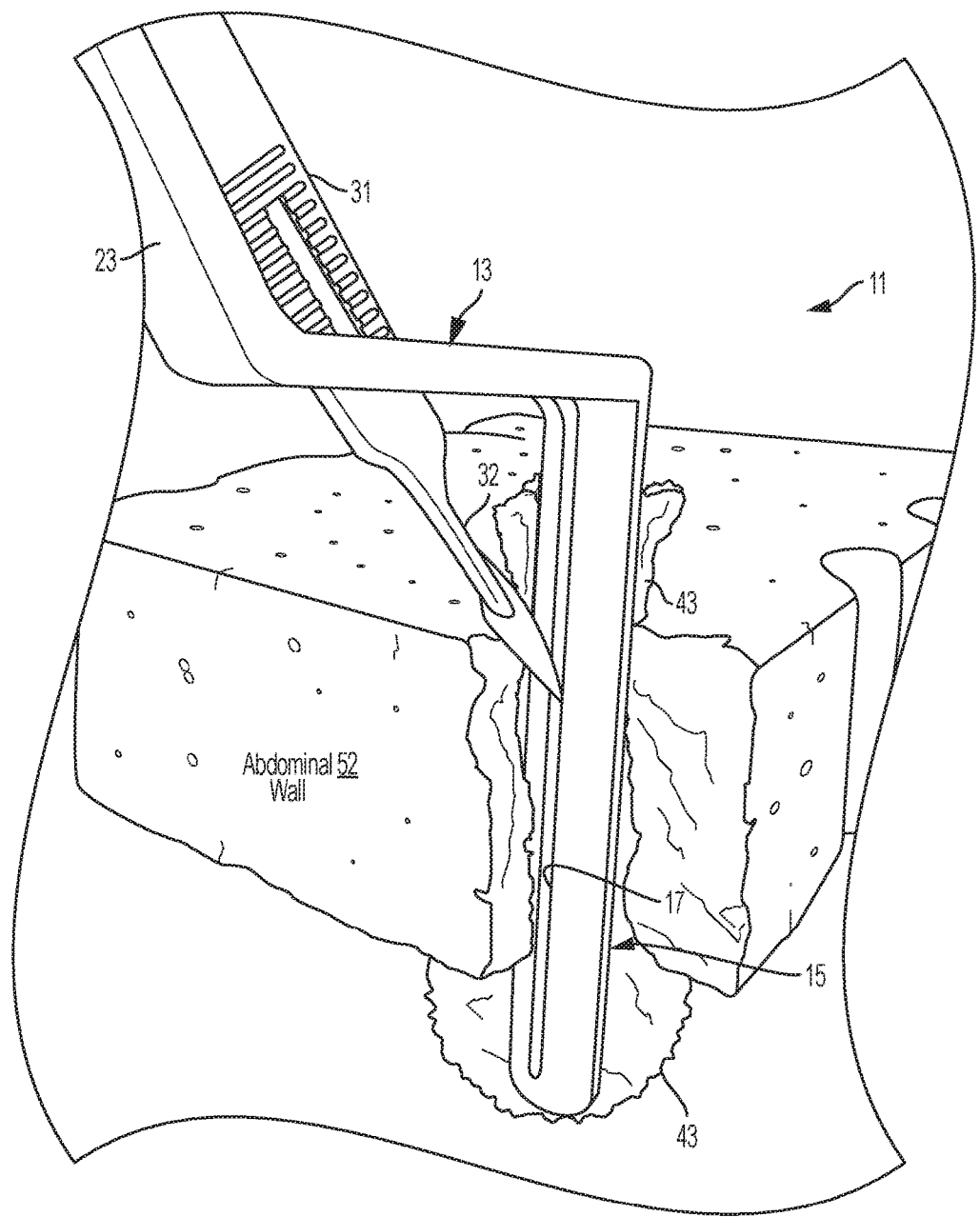
FIG. 11 provides a perspective side schematic view of an embodiment of the surgical retractor having a scalpel inserted through its aperture and in communication with its retention groove while the surgical retractor is inserted into an abdominal wall adjacent to a container or bag.

FIG. 11 provides a perspective side schematic view of an embodiment of the surgical retractor having a refraction member 11 that is shown with the use of surgical tool 31, such as a scalpel 32, inserted through its aperture of the proximal portion 13 while in communication with the retention guide 17 (e.g., groove) of the distal portion 15 (e.g., tongue or the like). The surgical retractor is being inserted (or has been inserted) into an abdominal wall 52 (or may be other types of cavity walls if applicable) and adjacent to a bag or container 43 that may contain an organ (or portion thereof), not shown.

Figure 12:
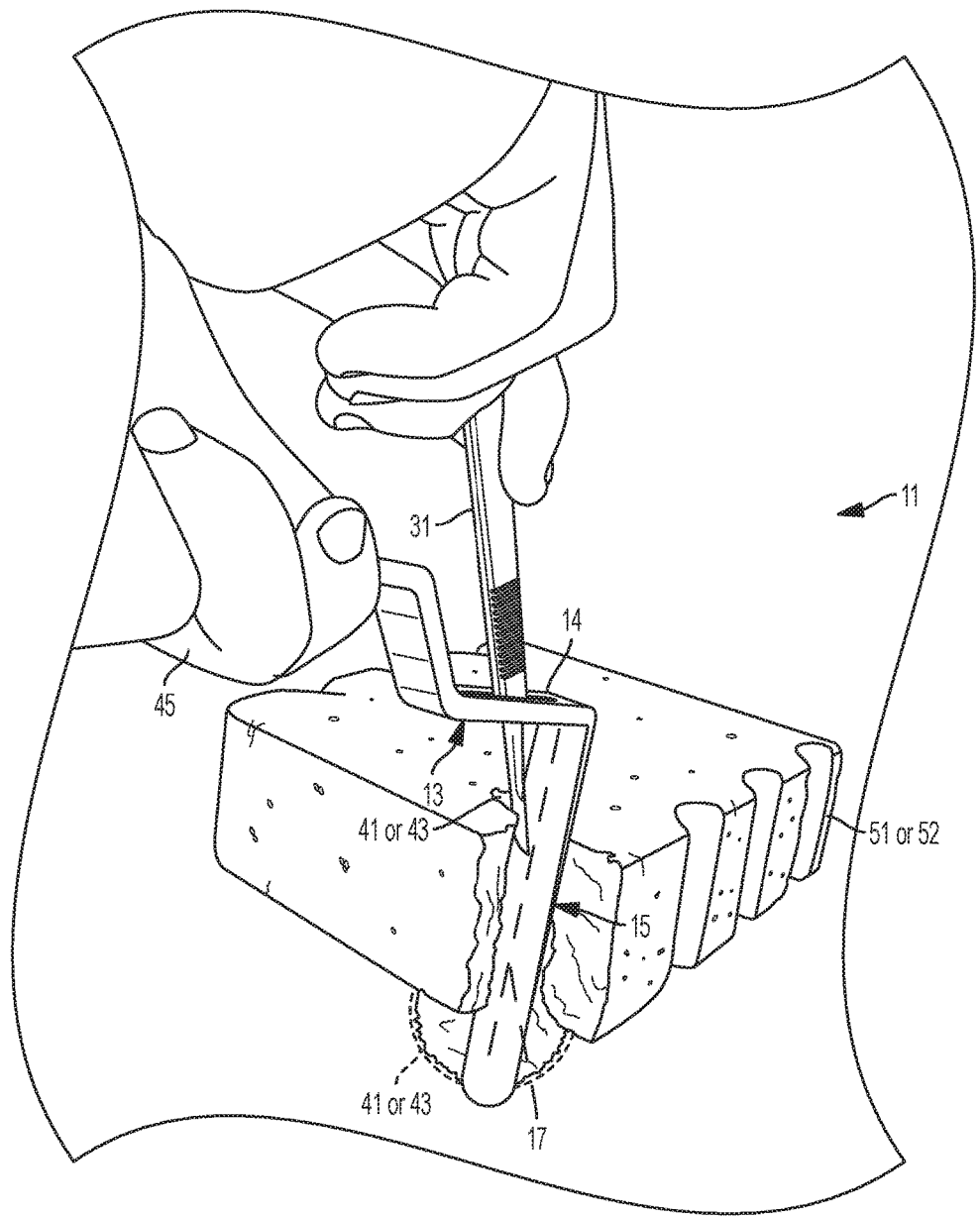
FIG. 12 provides a photographic depiction of perspective view of a user grasping an embodiment of the surgical refractor having a surgical tool inserted through its aperture and in communication with its retention groove while the surgical retractor is inserted into a model cavity wall or abdominal wall adjacent to a model container (or may be organ directly) for an organ.

FIG. 12 provides a photographic depiction of perspective view of a user 45 grasping an embodiment of the refraction member 11 of the surgical retractor having a surgical tool 31 inserted through its aperture 14 and in communication with its retention guide 17 (e.g., groove) while the surgical retractor is inserted into a model cavity wall 51 or abdominal wall 52 adjacent to a model container or bag 43 and/or an organ 41.

FIG. 13 provides a photographic depiction of perspective view of an embodiment of retraction member 11 of the surgical retractor having a surgical tool 31 inserted through its aperture and in communication with its retention guide 17 (e.g., groove) while the surgical retractor is inserted into a model cavity wall 51 and/or abdominal wall 52 adjacent to a model container or bag 43 and/or organ 41.

It should be appreciated that any of the distal portion, proximal portion, handles, offset portion, or any other segments, components, extensions, or structures associated with the various embodiments of the present invention surgical retractor device disclosed herein may be disposable or reusable; or some combination thereof.

It should be appreciated that any of the distal portion, proximal portion, handles, offset portion, or any other segments, components, extensions, or structures associated with the various embodiments of the present invention surgical retractor device disclosed herein may be a single integral unit or may be individually detachable and/or re-attachable; and any combination thereof.

It should be appreciated that any of the distal portion, proximal portion, handles, offset portion, or any other segments, components, extensions, or structures associated with the various embodiments of the present invention surgical retractor device disclosed herein may be expandable or retractable at the required location (respective to the anatomy, for example) or time (respective to the surgical procedure, for example).

It should be appreciated that as discussed herein, a subject may be a human or any animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to human (e.g. rat, dog, pig, monkey), etc. It should be appreciated that the subject may be any applicable human patient, for example.

It should be appreciated that various sizes, dimensions, contours, rigidity, shapes, flexibility and materials of any of the components or portions of components in the various embodiments discussed throughout may be varied and utilized as desired or required.

It should be appreciated that the practice of the various embodiments include, but not limited thereto, laparoscopic appendectomy, splenectomy, partial or total gastrectomy, nephrectomy, adrenalectomy, colectomy, enterectomy, esophagectomy, liver resection, oophorectomy, and pancreatectomy, as well as lung resections, removal of disease valves or other cardiac tissue, resections of other tissues from the thorax, or removal of tissue or organs from any body cavity. Embodiments also include use of small versions of the device in endoscopic joint surgery. It should be appreciated that the practice of the various embodiments include, but not limited thereto, endoscopic removal of organs or tissues from a body cavity, including thoracoscopic surgery, and removal of lung tissue, pleural masses, or other intrathoracic structures.

It should be appreciated that any bag, container, or the like and any of the organs, portions of organs, tissues, etc. discussed herein (and as desired or required) shall be considered a target region regarding the practice of various embodiment methods and devices.

It should be appreciated that the handle as well as other components of the retraction device may be sized (e.g., reduced or contoured, so as include a shorter handle) or provided a handle that can be held in place inside a hollow organ for Natural Orifice Translumenal Endoscopic Surgery (NOTES) procedures.

EXAMPLES

Practice of an aspect of an embodiment (or embodiments) of the invention will be still more fully understood from the following example set, which is presented herein for illustration only and should not be construed as limiting the invention in any way.

Examples Set No. 1

For instance, in a prototype a single-piece stainless steel surgical instrument, the purpose of which is to help remove impacted endoscopic recovery bags and organs and eliminate the risk of damaging the organ. An aspect of the prototype provides, a single-piece stainless steel surgical instrument consisting of a handle designed to be gripped in a single hand. The handle includes a curved end (catch) to provide an easy grip or leverage for a surgeon to hold. The handle is attached to a flat extension region (i.e., portion of a proximal portion) with a slot (or aperture) just wide enough to accommodate the width of a standard surgical scalpel handle (thereby providing a scalpel slot). The scalpel slot (aperture) is oriented along the midline of the flat extension region (i.e., portion of the proximal portion), beginning where the extension region meets the handle to the extreme end of the flat region opposite the handle, at the junction with a tongue (i.e., distal portion). In this prototype, the scalpel slot is approximately 37 mm long, and 5.1 mm wide. The function of the slot is to allow passage of the scalpel blade while preventing it from deviating from the perpendicular. To the end of the extension (i.e., portion of the proximal portion) is attached, at a right downward angle, a slightly concave—laterally—profile tongue (i.e., distal portion) of suitable length to span from the skin to the peritoneum of an obese patient or subject (100 mm long and 1.5 cm wide in the current embodiment). The concave "tongue" shape allows easy insertion through the trocar incision and promotes even retraction as tension is applied to the handle. The convex face of this tongue (distal portion) bears a narrow groove (retention groove) (approximately 2.5 mm wide and 1.2 mm deep in the current embodiment) that meets the scalpel aperture at the top. A purpose of the groove is to guide the tip of the scalpel blade as it is pushed through the abdominal wall (or other applicable cavity wall) when it is not possible to visualize the blade. The groove ends approximately 5 mm from the far tip of the tongue (i.e., distal portion) so that it will stop the passage of the scalpel at that point.

In application, the surgeon may use the prototype (or other applicable embodiment) when it is apparent that the gallbladder is too large to pull easily through the trocar site. The surgeon then pushes the insertion tongue into the patient or subject through the trocar incision, along one side of the gallbladder (typically along the side of the bag in which the gallbladder is held). The tip of the insertion tongue pushes the impacted gall bladder (or other organ) inside its endoscopic recovery bag slightly away from the abdominal wall. A scalpel is passed through the scalpel guide (aperture) with the tip of the scalpel blade in the groove (retention groove) on the back of the insertion tongue (distal portion), and with the sharp side of the scalpel blade facing away from the gallbladder and from the tongue (distal portion) of the retractor device. The tongue (distal portion) is then pushed down through the abdominal wall, while tension on the retractor device and gentle outward traction on the gallbladder (and bag) permits removal of the gallbladder as soon as the opening is just large enough to allow it. This step may be repeated if the gallbladder cannot be removed after a single passage of the scalpel. Multiple passages may be implemented if desired or required. The retractor device also may be removed, before the gallbladder and its bag are pulled through the enlarged incision. When properly used, the design of the retractor device mitigates the risk of accidentally cutting the recovery bag or organ as the incision is enlarged, and also keeps the opening occluded to prevent decompression of the abdominal cavity, thus keeping the abdominal wall and the blade used to extend the incision well away from abdominal contents.

Practice of an aspect of an embodiment (or embodiments) of the invention will be still more fully understood from the following experimental results, which are presented herein for illustration only and should not be construed as limiting the invention in any way.

Experimental Results Set No. 1

Evaluation of a Retraction Device for Gallbladder Extraction During Laparoscopic Cholecystectomy Objectives:
Primary Objectives:
1) To assess the safety of using a novel gallbladder extraction retractor during laparoscopic cholecystectomy.
2) To assess the utility of this device in extraction of difficult gallbladders during laparoscopic cholecystectomy as measured by surgeons opinion.
3) To determine time necessary to extract difficult gallbladders from the abdomen using a novel device for gallbladder extraction in laparoscopic cholecystectomy.
Secondary Objectives:
1) To estimate the proportion of operations in which the standard methods and tools for gallbladder extraction are inadequate or unsatisfactory.
2) To identify ways in which the gallbladder extraction retractor (GER) may be improved.
Design:
This is a single-institution pilot study seeking to evaluate whether the GER, designed to allow controlled extension of a laparoscopic incision while providing retraction and protection of the bag containing the gallbladder to be removed, is useful in extracting difficult to remove gallbladders from the patients once dissection of the gallbladder from the gallbladder fossa is complete in laparoscopic cholecystectomy. To avoid issues with possible conflict of interest we enlisted Dr. Peter Hallowell, MD, to serve as the study surgeon. He is a laparoscopic surgery expert with no involvement in the design process or financial interest in the project. He performed all procedures included in this study.

Regimen:
Patients who are scheduled to undergo laparoscopic cholecystectomy for biliary colic, choledocholithiasis and cholecystitis (acute or chronic) will be eligible for this study. All patients eligible will be offered the option of participating in the trial prior to their operation. They will then undergo laparoscopic cholecystectomy by the study surgeon and attempt at extraction of the gallbladder with the standard techniques. Some patients will not experience difficulty with the gallbladder extraction and will not require intervention using the study device. The operative time required to remove the gallbladder from the abdomen was recorded from the time the gallbladder bag is closed around the gallbladder. If the surgeon experiences difficulty with gallbladder extraction, defined as being unable to remove the extraction bag without an excessive amount of traction, the surgeon will then use the study device in removal. The operative time used in the removal of the gallbladder from the patient's abdomen once starting to use this GER will then be recorded. The operating surgeon will then score the ease of removal and satisfaction with the device on a Likert score based questionnaire and will note any difficulties encountered either with or without the device. Information will also be collected at the patient's post-operative visit regarding the presence or absence of any signs of infection at the incision sites and any issues with wound healing and with the cosmesis of the incision. Post procedure data of this kind was collected both for patients in whom the GER is used and for those in whom it is not used, however is not considered comparable, as their disease processes are dissimilar. A total of 20 patients in whom the GER is used will be enrolled in the study.

Interim Results:
Accrual: Thus far 14 patients have been enrolled. As addressed in the next paragraph, two patients have dropped out of the study prior to use of the device. Of the remaining patients, 8 of 12 total patients have required use of the device. Thus, device usage has been 66% in our study population, which is higher than the 20-30% initially expected. Our initial estimates of difficult gallbladder extraction were based on clinical experience and recall of the clinicians involved in the study, thus the disparity is not wholly unexpected. The increased usage represents increased need for this device.

Drop-out: One patient was removed from the study by the study surgeon intra-operatively, prior to the gallbladder extraction step. Concern was raised regarding the patient's safety due to a difficult dissection and perceived high risk for biliary injury and possible need for reconstruction as well as involvement of non-study personnel (hepatobiliary surgical consult). Given the complicated nature of this case, the study surgeon elected to remove the patient from the study prior to any consideration of device usage, in accordance with the exclusion criteria in the study protocol. One other patient signed a consent form to participate and later withdrew her consent, prior to her surgical date.

Follow-up: Follow-up data is available for all patients except two, one in whom the device was used, and one in whom it was not used.

Adverse Events: No adverse events have been recorded for either group of patients in this trial. This includes both intra-operative and post-operative adverse events.

Data for Patients Who Required Use of the Device:

Indication and Time for Removal—The following table displays the time elapsed from the initial attempt to remove the specimen bag from the abdomen until the decision is made to use the device. Time for removal using the device is also displayed.

TABLE 1

| Subject # | Indication for Operation | Time until decision to use device, in minutes:seconds | Time for removal (with device) in minutes;seconds |
|---|---|---|---|
| 1 | Chronic Cholecystitis | 0:46 | 1:04 |
| 6 | Biliary Colic | 0:12 | 2:24 |
| 7 | Choledocholithiasis | 1:00 | 0:27 |
| 9 | Biliary Colic | 0:05 | 1:10 |
| 10 | Biliary Colic | 0:30 | 1:01 |
| 11 | Chronic Cholecystitis with hydrops | 0:22 | 6:56 |
| 12 | Biliary Colic | 0:23 | 1:50 |
| 13 | Chronic Cholecystitis | 0:12 | 1:09 |

Utility Scores—The following table displays utility scores assigned by the study surgeon, Dr. Peter Hallowell immediately following each operation.

TABLE 2

| Patient Consent number | Overall Utility | Insertion/positioning | Extension and groove guide | Retraction sturdiness | Specimen removal | Blade Removal |
|---|---|---|---|---|---|---|
| 1 | 2 | 1 | 2 | 1 | 2 | 1 |
| 6 | 2 | 2 | 2 | 1 | 1 | 1 |
| 7 | 1 | 2 | 2 | 1 | 1 | 1 |
| 9 | 1 | 1 | 1 | 1 | 2 | 1 |
| 10 | 1 | 2 | 1 | 1 | 1 | 1 |
| 11 | 2 | 1 | 1 | 1 | 3 | 1 |
| 12 | 2 | 1 | 2 | 1 | 3 | 1 |
| 13 | 1 | 1 | 2 | 1 | 2 | 1 |
| average | 1.5 | 1.4 | 1.6 | 1 | 1.8 | 1 |

Score are based on scale from 1 (outstanding benefit) to 5 (hindrance to procedure)

Post-operative Assessment Data—The following table displays data on cosmetic result as assessed by the study surgeon and the patient, as well as global post-operative pain rating and if any suspicion for infection was present.

TABLE 3

| Subject # | Cosmesis - surgeon assessment | Cosmesis - patient assessment | Pain rating | Suspicion of infection? |
|---|---|---|---|---|
| 1 | 1 | 1 | 2 | N |
| 6 | 1 | 1 | 1 | N |
| 7 | 3 | 2 | 1 | N |
| 9 | 1 | 1 | 2 | N |
| 10 | 1 | 1 | 2 | N |
| 11 | 1 | 1 | 2 | N |
| 12 | N/A | N/A | N/A | N/A |
| 13 | 1 | 1 | 3 | N |
| average | 1.4 | 1.2 | 1.6 | — |

Score are based on scale from 1 (excellent result) to 5 (poor result). Patient 12 has not yet had a follow-up visit.

Data for Patients not Requiring the Device:

Data for patients who did not require the device is displayed in the table below.

TABLE 4

| Subject # | Indication | Time required for removal | Cosmesis - Surgeon | Cosmesis - Patient | Post-op Pain rating | Suspicion of Infection | Comments |
|---|---|---|---|---|---|---|---|
| 2 | Biliary Colic | 0:04 | NR | NR | NR | NR | Never Followed-up, possibly moved. |
| 3 | Biliary Colic | 0:31 | 1 | 1 | 1 | N | |
| 4 | Biliary Colic | NR | 1 | 1 | 2 | N | |
| 5 | N/A | N/A | N/A | N/A | N/A | N/A | Taken off study |
| 8 | Biliary Colic | 0:03 | 1 | 1 | 1 | N | |

NR = Not recorded, Time given in minutes:seconds, ratings on a scale from 1 (best outcome) to 5 (poor outcome).

Conclusions: Several conclusions can be drawn from our preliminary data. First, it appears that in our center, the proportion of patients in which gallbladder extraction is difficult is much higher than initially postulated. This may be explained by our position as an academic medical center and tertiary referral center but may also indicate that this problem is more common than initially suspected. Second, it appears that difficult extraction can be recognized in an expeditious fashion. Often it is the case that the surgeon can expect difficult extraction based on early intra-operative findings and initial inspection of the gallbladder. Also, the size mismatch is readily apparent once gallbladder extraction is attempted, often within the first few seconds of the attempt.

Regarding the performance of the device, in 7 of the 12 cases in which the device was used, extraction took less than 2 minutes. In the case with the longest extraction, the incision was not optimally oriented for extension into the umbilicus. A resident who was not familiar with the device made the initial incision transversely rather than vertically. Though the device will work in with a transverse incision, the study surgeon has experienced better outcomes with a vertical incision. It would appear that in the majority of cases, the device has been used expeditiously. It should be noted that this group in whom the device has been used is not comparable to those in which it has not, as this is not a randomized trial and those in whom the device has not been used do not have the gallbladder/incision size mismatch present in the first group. Also of note, the devices made to updated specifications have not been put into practice yet.

Surgeon acceptance of the device has been good, and the scores appear to indicate the surgeon believes that the device is of benefit.

Further, it should be kept in mind that the two cohorts of patients (those in whom the device is used, and those in whom it is not) are not comparable as their disease process is different. This was not a randomized study, but rather a pilot study to gain some initial data and familiarity with the device's use.

Additional Examples

Example 1 includes an apparatus comprising: a surgical retractor device for insertion through an incision in a cavity wall of a subject for use with a surgical tool, the surgical retractor device comprising: a retraction member having a proximal portion and a distal portion; the proximal portion comprising an aperture in communication therewith, the aperture configured to accommodate at least a portion of the surgical tool for insertion there through; and the distal portion configured to protect a target region of the subject by blocking and displacing the target region away from the surgical tool to be passed through the proximal portion aperture.

Example 2 may optionally include the apparatus of example 1, wherein the distal portion comprises a first surface and a second surface, and wherein the distal portion comprises a retention guide in communication with the distal portion first surface and configured to receive and guide the portion of the surgical tool inserted through the proximal portion aperture.

Example 3 may optionally include the apparatus of example 2, further comprising a check structure in communication with the retention guide, wherein the check structure is configured to contact the surgical tool traveling along the retention guide, wherein the contact provides feedback to the user of corresponding location of the surgical tool.

Example 4 may optionally include the apparatus of example 3, wherein the retention guide comprises a first side wall and a second side wall, and wherein at least one the check structure is disposed on one or both of the retention guide first side wall and second side wall.

Example 5 may optionally include the apparatus of example 4, wherein the check structure comprises any combination of at least one of: ridge, bump, lip, ledge, tab, notch, and indentation.

Example 6 may optionally include the apparatus of example 2 (as well as subject matter of one or more of any combination of examples 1-5) wherein the distal portion retention guide has a configuration to prevent the surgical tool from contacting the target region.

Example 7 may optionally include the apparatus of example 2 (as well as subject matter of one or more of any combination of examples 1-6), wherein the proximal portion aperture is aligned with the distal portion retention guide so as to be able to concurrently accommodate the inserted portion of the surgical tool in the proximal portion aperture and the distal portion retention guide.

Example 8 may optionally include the apparatus of example 7 (as well as subject matter of one or more of any combination of examples 1-6), wherein the retention guide comprises a groove, slot, track, or channel.

Example 9 may optionally include the apparatus of example 7 (as well as subject matter of one or more of any combination of examples 1-6), wherein the retention guide comprises a trolley mechanism in communication with the distal portion, wherein the trolley mechanism is configured to travel in communication along the distal portion.

Example 10 may optionally include the apparatus of example 1 (as well as subject matter of one or more of any combination of examples 1-9), wherein the proximal portion and the distal portion configured to guide and extend the incision of the cavity wall, wherein the cavity wall comprises: an abdominal wall, pelvic wall, or thoracic wall.

Example 11 may optionally include the apparatus of example 1 (as well as subject matter of one or more of any combination of examples 1-10), wherein the surgical incision is a type provided by one of the following surgical procedure types: laparoscopic, thoracic, or endoscopic.

Example 12 may optionally include the apparatus of example 1 (as well as subject matter of one or more of any combination of examples 1-11), wherein the surgical tool comprises at least one of: scalpel, other cutting instrument, cautery instrument, and needle.

Example 13 may optionally include the apparatus of example 1 (as well as subject matter of one or more of any combination of examples 1-12), wherein the distal portion comprises a first surface and a second surface, and wherein the second surface substantially having a laterally concave shaped surface.

Example 14 may optionally include the apparatus of example 1 (as well as subject matter of one or more of any combination of examples 1-13), further comprising an adhesion structure disposed on the first surface of the distal portion configured to increase adhesion of the distal portion first surface to the cavity wall.

Example 15 may optionally include the apparatus of example 14 (as well as subject matter of one or more of any combination of examples 1-14), wherein the adhesion structure comprises at least one of: ridges, textured surface, bumps, protrusions, and jagged surface.

Example 16 may optionally include the apparatus of example 1 (as well as subject matter of one or more of any combination of examples 1-15), wherein the proximal portion having a longitudinal alignment and the distal portion having a longitudinally alignment wherein their respective longitudinal alignments define a general angle of less than 180 degrees.

Example 17 may optionally include the apparatus of example 1 (as well as subject matter of one or more of any combination of examples 1-16), wherein the proximal portion having a longitudinal alignment and the distal portion having a longitudinally alignment wherein their respective longitudinal alignments define a general angle of less than 90 degrees.

Example 18 may optionally include the apparatus of example 1 (as well as subject matter of one or more of any combination of examples 1-17), wherein the proximal portion having a longitudinal alignment and the distal portion having a longitudinally alignment wherein their respective longitudinal alignments define a general angle of about 90 degrees.

Example 19 may optionally include the apparatus of example 1 (as well as subject matter of one or more of any combination of examples 1-18), wherein the proximal portion further comprises a handle.

Example 20 may optionally include the apparatus of example 19 (as well as subject matter of one or more of any combination of examples 1-18), wherein the handle comprises a catch disposed proximally from the distal portion, wherein the catch is configured to help user grasp the handle.

Example 21 may optionally include the apparatus of example 20 (as well as subject matter of one or more of any combination of examples 1-19), wherein the proximal portion further comprises an offset member.

Example 22 may optionally include the apparatus of example 21 (as well as subject matter of one or more of any combination of examples 1-20), wherein the offset member extends between (1) the proximal portion comprising the aperture in communication therewith and (2) the handle, wherein the handle is generally parallel to but offset from the proximal portion comprising the aperture.

Example 23 may optionally include the apparatus of example 1 (as well as subject matter of one or more of any combination of examples 1-22), wherein the proximal portion further comprises an offset member.

Example 24 may optionally include the apparatus of example 1 (as well as subject matter of one or more of any combination of examples 1-23), wherein the proximal portion aperture is disposed in the proximal portion.

Example 25 may optionally include the apparatus of example 1 (as well as subject matter of one or more of any combination of examples 1-24), wherein the proximal portion aperture is disposed adjacent to the proximal portion.

Example 26 may optionally include the apparatus of example 1 (as well as subject matter of one or more of any combination of examples 1-25), further comprising the surgical tool provided together in a kit with the surgical retractor device.

Example 27 may optionally include the apparatus of example 26 (as well as subject matter of one or more of any combination of examples 1-25), wherein the proximal portion aperture is configured to prevent the surgical tool from traveling beyond the distal portion so as to prevent the surgical tool from contacting the target region.

Example 28 may optionally include the apparatus of example 26 (as well as subject matter of one or more of any combination of examples 1-26), wherein the proximal portion aperture is configured to prevent the surgical tool from traveling laterally pass either side of the distal portion.

Example 29 may optionally include the apparatus of example 26 (as well as subject matter of one or more of any combination of examples 1-28), wherein the surgical tool is configured respective to the proximal portion aperture to prevent the surgical tool from traveling beyond the distal portion so as to prevent the surgical tool from contacting the target region.

Example 30 may optionally include the apparatus of example 26 (as well as subject matter of one or more of any combination of examples 1-29), wherein the surgical tool is configured respective to the proximal portion aperture to prevent the surgical tool from traveling laterally pass either side of the distal portion.

Example 31 may optionally include the device of example 26 (as well as subject matter of one or more of any combination of examples 1-30), wherein the surgical tool comprises at least one of: scalpel, other cutting instrument, cautery instrument, and needle.

Example 32 includes a method for inserting a surgical refractor device through an incision in a cavity wall of a subject for use with a surgical tool, the method comprising: obtaining or providing the surgical retractor device that includes a retraction member having a proximal portion and a distal portion, wherein the proximal portion comprises an aperture in communication therewith, and wherein the distal portion is configured to protect a target region of the subject by blocking and displacing the target region away from the surgical tool to be passed through the proximal portion aperture; inserting at least a portion of the surgical tool through the proximal portion aperture; and using the distal portion for blocking and displacing the target region away from the portion of the surgical tool that is passed through the proximal portion aperture.

Example 33 may optionally include the method of example 32 (as well as subject matter of one or more of any combination of examples 1-31), comprising:
using the distal portion for guiding a portion of the surgical tool that is inserted through the proximal portion aperture.

Example 34 may optionally include the method of example 33 (as well as subject matter of one or more of any combination of examples 1-32), wherein the guiding of the portion of the surgical tool comprises retaining the portion of the surgical tool as it travels in communication with the distal portion.

Example 35 may optionally include the method of example 33 (as well as subject matter of one or more of any combination of examples 1-34), further comprising: obtaining or providing a user indication of the corresponding location of the surgical tool along the distal portion.

Example 36 may optionally include the method of example 33 (as well as subject matter of one or more of any combination of examples 1-35), further comprising using the distal portion to inhibit or prevent the surgical tool that is inserted though the proximal aperture and traveling along the distal portion from contacting the organ.

Example 37 may optionally include the method of example 33 (as well as subject matter of one or more of any combination of examples 1-36), wherein the proximal portion aperture and the distal portion are aligned with one another so as to be able to concurrently accommodate the inserted surgical tool in the proximal portion aperture and in communication with the distal portion.

Example 38 may optionally include the method of example 32 (as well as subject matter of one or more of any combination of examples 1-37), further comprising: guiding and extending the incision of the cavity wall, wherein the cavity wall comprises: an abdominal wall, pelvic wall, or thoracic wall.

Example 39 may optionally include the method of example 32 (as well as subject matter of one or more of any combination of examples 1-38), wherein the target region is an organ.

Example 40 may optionally include the method of example 39 (as well as subject matter of one or more of any combination of examples 1-38), wherein the organ is disposed in a bag or container.

Example 41 may optionally include the method of example 39 (as well as subject matter of one or more of any combination of examples 1-40), wherein at least a portion of the organ is disposed in a bag or container.

Example 42 may optionally include the method of example 32 (as well as subject matter of one or more of any combination of examples 1-41), wherein the surgical incision is a type provided by one of the following surgical procedure types: laparoscopic, thoracic, or endoscopic.

Example 43 may optionally include the method of example 32 (as well as subject matter of one or more of any combination of examples 1-42), wherein the surgical tool comprises at least one of: scalpel, other cutting instrument, cautery instrument, and needle.

Example 44 may optionally include the method of example 32 (as well as subject matter of one or more of any combination of examples 1-43), further comprising: adhering of the distal portion to the cavity wall by providing an adhesion structure disposed on the first surface of the distal portion.

Example 45 may optionally include the method of example 32, further comprising: grasping or manipulating the surgical retractor device by use of a handle or other extension member that is in communication with the proximal portion.

Example 46 may optionally include the method of example 32 (as well as subject matter of one or more of any combination of examples 1-45), further comprising: providing the surgical tool to form a kit with the surgical retractor device.

Example 47 may optionally include the method of example 46 (as well as subject matter of one or more of any combination of examples 1-45), wherein the surgical tool comprises at least one of: scalpel, other cutting instrument, cautery instrument, and needle.

Example 48 may optionally include (as well as subject matter of one or more of any combination of examples 1-31) the apparatus comprising: a surgical tool; and a surgical retractor device for insertion through an incision in a cavity wall of a subject, the surgical retractor device comprising: a retraction member having a proximal portion and a distal portion; the proximal portion comprising an aperture in communication therewith, the aperture configured to accommodate at least a portion of the surgical tool for insertion there through; and the distal portion configured to protect a target region of the subject by blocking and displacing the target region away from the surgical tool to be passed through the proximal portion aperture.

Example 49 may optionally include (as well as subject matter of one or more of any combination of examples 1-31 and/or 32-47) the apparatus comprising: a surgical retractor device for insertion through an incision in a cavity wall of a subject for use with a surgical tool, the surgical retractor device comprising: a retraction member having a proximal portion and a distal portion; the proximal portion comprising an insertion guide in communication therewith, the insertion guide configured to accommodate at least a portion of the surgical tool for insertion there through; and the distal portion configured to protect a target region of the subject by blocking and displacing the target region away from the surgical tool to be passed through the proximal portion aperture.

Example 50 may optionally include the apparatus of example 49, wherein the distal portion comprises a first surface and a second surface, and wherein the distal portion comprises a retention guide in communication with the distal portion first surface and configured to receive and guide the portion of the surgical tool inserted through the proximal portion aperture.

Example 51 may optionally include the apparatus of example 50, wherein the distal portion retention guide has a configuration to prevent the surgical tool from contacting the target region.

Example 52 may optionally include the apparatus of example 50, wherein the proximal portion insertion guide is aligned with the distal portion retention guide so as to be able to concurrently accommodate the inserted portion of the surgical tool in the proximal portion insertion guide and the distal portion retention guide. Example 53 may optionally include the apparatus of example 49, further comprising the surgical tool provided together in a kit with the surgical retractor device.

Example 54 may optionally include the apparatus of example 49, wherein the proximal portion insertion guide comprises an aperture.

Example 55 may optionally include the apparatus of example 49, wherein the proximal portion insertion guide comprises a recess, post, tab, hook, notch, cut, slot, holder or socket configured to control the movement of the surgical tool relative to the surgical retractor device.

Example 56 may include a method of manufacturing the apparatus or surgical retractor device (including the various combinations of the related components, structures, portions and mechanisms thereof) according to any one or more of Examples 1-55.

The devices, systems, compositions, computer program products, and methods of various embodiments of the invention disclosed herein may utilize aspects disclosed in the following references, applications, publications and patents and which are hereby incorporated by reference herein in their entirety:

1. U.S. Pat. No. 7,220,228 B2, Hu, et al., "Surgical Refractor Blade and System", May 22, 2007.

2. U.S. Pat. No. 5,522,791, Leyva, H., "Apparatus for Retracting an Incision and Inflating an Abdominal Cavity", Jun. 4, 1996.

3. U.S. Patent Application Publication No. US 2006/0189848 A1, Peneberg, B., "Surgical Retractor with Attachment", Aug. 24, 2006; U.S. patent application Ser. No. 11/354,537, filed Feb. 15, 2006.

4. U.S. Patent Application Publication No. US 2006/0063978 A1, Ritland, S., "Opposing Parallel Bladed Retractor and Method of Use", Mar. 23, 2006; U.S. patent application Ser. No. 11/228,106, filed Sep. 16, 2005.

5. U.S. Patent Application Publication No. US 2004/0254428 A1, Ritland, S., "Intermuscular Guide for Retractor Insertion and Method of Use", Dec. 16, 2004.

6. U.S. Pat. No. 4,836,190, Zwick, C., "Visceral Retractor", Jun. 6, 1989.

7. U.S. Pat. No. 5,351,680, Jung, H., "Surgical Retractor", Oct. 4, 1994.

8. U.S. Pat. No. 5,667,519, Ramsey, D., "Knife for Laparoscopic Surgery", Sep. 16, 1997.

9. U.S. Pat. No. 6,007,554, Van Ess, L., "Surgical Cutter", Dec. 28, 1999.

10. U.S. Pat. No. 4,945,497, Greenstein, et al., "Surgical Retractor", Aug. 7, 1990.

11. U.S. Pat. No. 7,396,328 B2, Peneberg, B., "Surgical Retractors with Attachment", Jul. 8, 2008.

12. U.S. Design Pat. No. D568,471 S, Engler, A., "Implant Retractor", May 6, 2008.

13. U.S. Pat. No. 6,7321,739 B2, Cosgrove, D., "Minimally Invasive Cardiac Surgery Procedure", May 11, 2004.

14. U.S. Pat. No. 6,554,768 B1, Leonard, R., "Illuminated Deep Pelvic Refractor", Apr. 29, 2003.

15. U.S. Pat. No. 6,416,465 B2, Brau, S., "Surgical Retractor and Related Surgical Approach to Access the Anterior Lumbar Region", Jul. 9, 2002.

16. U.S. Pat. No. 5,558,621, Heil, T., "Surgical Retractor with Cross Bar Grips", Sep. 24, 1996.

17. U.S. Pat. No. 5,514,077, Rabban, P., "Surgical Retractor", May 7, 1996.

18. U.S. Pat. No. 4,610,243, Ray, C., "Malleable Force-Fulcrum Retractor", Sep. 9, 1986.

19. U.S. Pat. No. 2,863,444, Winsten, J., "Liver Retractor for Cholecystectomies", Dec. 9, 1958.

20. U.S. Pat. No. 1,465,259, Friedman, H., "Dental Apparatus", Aug. 21, 1923.

21. U.S. Pat. No. 659,182, Pilling, C. J., "Retractor", Oct. 2, 1900.

22. U.S. Pat. No. 5,375,591, Mouret, P., "Instrument for Implementing Medical or Surgical Operations by Laparoscopy or Coeliscoopy", Dec. 27, 1994.

23. Olsen D O. Laparoscopic cholecystectomy. *The American Journal of Surgery* 1991; 161(3):339-344.

24. Sarli L, Contini S, Sansebastiano G, Gobbi S, Costi R, Roncoroni L. Does Laparoscopic Cholecystectomy Worsen the Prognosis of Unsuspected Gallbladder Cancer? *Arch Surg* 2000; 135(11):1340-1344.

25. Wullstein C, Woeste G, Barkhausen S, Gross E, Hopt U. Do complications related to laparoscopic cholecystectomy influence the prognosis of gallbladder cancer? *Surgical Endoscopy* 2002; 16(5):828-832.

26. Kim J, Kim W, Kim J, Yoo B, Kim M. Unsuspected Gallbladder Cancer Diagnosed After Laparoscopic Cholecystectomy: Focus on Acute Cholecystitis. *World Journal of Surgery* 2010; 34(1):114-120.

27. Bordelon B, Hobday K, Hunter J. Incision extension is the optimal method of difficult gallbladder extraction at laparoscopic cholecystectomy. *Surgical Endoscopy* 1992; 6(5):225-227.

In summary, while the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the following claims, including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

We claim:

1. An apparatus comprising:
    a surgical retractor device for receiving a surgical tool, said surgical retractor device comprising:
        a retraction member having a proximal portion and a distal portion, said distal portion configured for insertion through an incision in a cavity wall and into a cavity of a subject, wherein:
            said cavity wall is an abdominal wall, pelvic wall, or thoracic wall, and said cavity is an abdominal cavity, a pelvic cavity, or a thoracic cavity, respectively;
        said proximal portion comprising an aperture disposed in said proximal portion, said aperture configured to accommodate at least a portion of the surgical tool for insertion there through said aperture;
        said distal portion comprises a first surface and a second surface, said distal portion being a tongue-like shape that when the surgical tool is passed through said aperture, said distal portion's second surface is configured to block and displace an organ in the cavity of the subject away from the surgical tool to protect the organ of the subject; and
        wherein said distal portion comprises a retention guide disposed on said distal portion's first surface and wherein said retention guide has a configuration configured to receive and guide the portion of the surgical tool, which is inserted through the aperture, for a travel along the retention guide disposed on the distal portion's first surface to prevent the surgical tool from contacting the organ.

2. The apparatus of claim 1, further comprising a check structure in communication with said retention guide, wherein said check structure is configured to contact the surgical tool traveling along said retention guide, wherein said contact provides feedback to the user of corresponding location of the surgical tool.

3. The apparatus of claim 2, wherein said retention guide comprises a first side wall and a second side wall, and wherein at least one said check structure is disposed on one or both of said retention guide first side wall and second side wall.

4. The apparatus of claim 3, wherein said check structure comprises any combination of at least one of: ridge, bump, lip, ledge, tab, notch, and indentation.

5. The apparatus of claim 1, wherein said proximal portion aperture is aligned with said distal portion retention guide so as to be able to concurrently accommodate the inserted portion of the surgical tool in said proximal portion aperture and said distal portion retention guide.

6. The apparatus of claim 5, wherein said retention guide comprises a groove, slot, track, or channel.

7. The apparatus of claim 5, wherein said retention guide comprises a trolley mechanism, wherein said trolley mechanism is configured to travel in communication along said distal portion.

8. The apparatus of claim 1, wherein said proximal portion and said distal portion configured to guide and extend the incision of the cavity wall.

9. The apparatus of claim 1, wherein the surgical incision is a type provided by one of the following surgical procedure types: laparoscopic, thoracic, or endoscopic.

10. The apparatus of claim 1, wherein the surgical tool comprises at least one of: scalpel, other cutting instrument, cautery instrument, and needle.

11. The apparatus of claim 1, wherein said distal portion's second surface substantially having a laterally concave shaped surface.

12. The apparatus of claim 1, further comprising an adhesion structure disposed on said first surface of said distal portion configured to increase adhesion of the distal portion first surface to said cavity wall.

13. The apparatus of claim 12, wherein said adhesion structure comprises at least one of: ridges, textured surface, bumps, protrusions, and jagged surface.

14. The apparatus of claim 1, wherein said proximal portion having a longitudinal alignment and said distal portion having a longitudinal alignment wherein their respective longitudinal alignments define a general angle of less than 180 degrees.

15. The apparatus of claim 1, wherein said proximal portion having a longitudinal alignment and said distal portion having a longitudinal alignment wherein their respective longitudinal alignments define a general angle of less than 90 degrees.

16. The apparatus of claim 1, wherein said proximal portion having a longitudinal alignment and said distal portion having a longitudinal alignment wherein their respective longitudinal alignments define a general angle of about 90 degrees.

17. The apparatus of claim 1, wherein said proximal portion further comprises a handle.

18. The apparatus of claim 17, wherein said handle comprises a catch disposed proximally from said distal portion, wherein said catch is configured to help user grasp said handle.

19. The apparatus of claim 18, wherein said proximal portion further comprises an offset member.

20. The apparatus of claim 19, wherein said offset member extends between (1) said proximal portion comprising said aperture disposed therein and (2) said handle, wherein said handle is generally parallel to but offset from said proximal portion comprising said aperture.

21. The apparatus of claim 1, wherein said proximal portion further comprises an offset member.

22. The apparatus of claim 1, wherein said proximal portion aperture is disposed substantially in the center, laterally, of said proximal portion.

23. The apparatus of claim 1, wherein said proximal portion aperture is disposed substantially off-center, laterally, of said proximal portion.

24. The apparatus of claim 1, further comprising said surgical tool provided together in a kit with said surgical retractor device.

25. The apparatus of claim 24, wherein said proximal portion aperture is configured to prevent said surgical tool from traveling beyond said distal portion so as to prevent said surgical tool from contacting the organ.

26. The apparatus of claim 24, wherein said proximal portion aperture is configured to prevent said surgical tool from traveling laterally pass either side of said distal portion.

27. The apparatus of claim 24, wherein said surgical tool is configured respective to said proximal portion aperture to prevent said surgical tool from traveling beyond said distal portion so as to prevent the surgical tool from contacting the organ.

28. The apparatus of claim 24, wherein said surgical tool is configured respective to said proximal portion aperture to prevent said surgical tool from traveling laterally pass either side of said distal portion.

29. The device of claim 24, wherein the surgical tool comprises at least one of: scalpel, other cutting instrument, cautery instrument, and needle.

* * * * *